United States Patent [19]
Kroin et al.

[11] Patent Number: 5,776,939
[45] Date of Patent: Jul. 7, 1998

[54] DRUG RESISTANCE AND MULTIDRUG RESISTANCE MODULATORS

[75] Inventors: Julian Stanley Kroin; Bryan Hurst Norman, both of Indianapolis, Ind.

[73] Assignee: Eli Lilly and Company, Indianapolis, Ind.

[21] Appl. No.: 873,583

[22] Filed: Jun. 12, 1997

[51] Int. Cl.$^6$ .................. A01N 43/60; C07D 241/04
[52] U.S. Cl. .................................. 514/255; 544/381
[58] Field of Search ................. 544/381; 514/255

[56] References Cited

U.S. PATENT DOCUMENTS

| | | |
|---|---|---|
| 5,112,817 | 5/1992 | Fukazawa et al. |
| 5,523,304 | 6/1996 | Sunkara |
| 5,596,002 | 1/1997 | Hofheinz et al. |
| 5,654,304 | 8/1997 | Pfister et al. .................. 514/253 |

FOREIGN PATENT DOCUMENTS

| | | | |
|---|---|---|---|
| WO 93/17021 | 9/1993 | WIPO | C07D 473/16 |
| WO 94/22842 | 10/1994 | WIPO | C07D 261/08 |
| WO 94/24107 | 10/1994 | WIPO | C07D 215/20 |

OTHER PUBLICATIONS

Ruetz, Stephan, et al., "The pfmdr1 gene of *Plasmodium falciparum* confers cellular resistance to antimalarial drugs in yeast cells," Proc. Natl. Acad. Sci. USA, vol. 93, pp. 9942–9947, (1996).

Terao, Toshimitsu, et al., "Active Secretion of Drugs from the Small Intestinal Epithelium in Rats by P–Glycoprotein Functioning as an Absorption Barrier," *J. Pharm. Pharmacol*, 48:1083–1089 (1996).

Pfister, J. R., et al., "Methanodibenzosuberylpiperazines as Potent Multidrug Resistance Reversal Agents," *Bioorganic & Medicinal Chemistry Letters*, vol. 5, No. 21, pp. 2473–2476 (1995).

*Primary Examiner*—Mukund J. Shah
*Assistant Examiner*—Tamthom T. Ngo
*Attorney, Agent, or Firm*—Robert A. Conrad; David E. Boone

[57] ABSTRACT

Drug and multidrug resistant modulators of Formula (C):

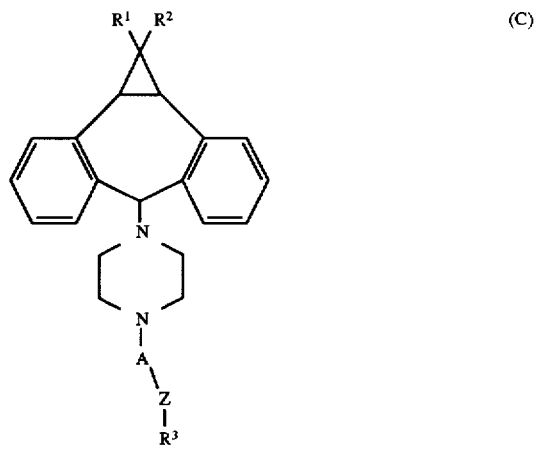

where Z is selected from the group consisting of —S—, —S(O)$_w$—, and —CH$_2$—, where w is 1 or 2; and pharmaceutically acceptable salts or solvates thereof are described and claimed.

Use of the new compounds in the preparation of pharmaceutical compositions is described and claimed. In addition, methods for treating drug and multidrug resistance in various diseases using a compound of this invention are described and claimed. Also, methods of enhancing oral bioavailability of a drug and methods of enhancing bioavailability of a drug to the brain using a compound of this invention are described and claimed.

18 Claims, No Drawings

DRUG RESISTANCE AND MULTIDRUG RESISTANCE MODULATORS

FIELD OF THE INVENTION

This invention relates to the field of synthetic organic chemistry. Specifically, the invention relates to pharmaceutical compounds that are useful in the field of drug resistance and multidrug resistance.

BACKGROUND OF THE INVENTION

Among the problems faced in certain types of drug therapy, including cancer chemotherapy and malaria drug therapy, is the phenomena of resistance to treatment regimens. The resistance means, for example, that cancerous tumors that have responded well initially to a particular drug or drugs, later develop a tolerance to the drug(s) and cease responding. Drug resistance is the name given to the circumstance when a disease (e.g., malaria or cancer) does not respond to a treatment drug or drugs. Drug resistance can be either intrinsic, which means the disease has never been responsive to the drug or drugs, or it can be acquired, which means the disease ceases responding to a drug or drugs to which the disease had previously been responsive. Multidrug resistance is a specific type of drug resistance that is characterized by cross-resistance of a disease to more than one functionally and/or structurally unrelated drugs. Multidrug resistance, in the field of cancer, is discussed in greater detail in "Detoxification Mechanisms and Tumor Cell Resistance to Anticancer Drugs," by Kuzmich and Tew, particularly section VII "The Multidrug-Resistant Phenotype (MDR)," *Medical Research Reviews*, Vol. 11, No. 2, 185–217, (Section VII is at pp. 208–213) (1991); and in "Multidrug Resistance and Chemosensitization: Therapeutic Implications for Cancer Chemotherapy," by Georges, Sharom and Ling, Advances in Pharmacoloay, Vol. 21, 185–220 (1990).

Treatment of drug and multidrug resistance typically involves the coadministration of a drug suitable for treatment of the disease and a compound known as a drug resistance modulator or a multidrug resistance modulator. Drug and multidrug resistance modulators act through various mechanisms to cause a drug or drugs suitable for treatment of a disease to begin and/or continue to function as a therapeutic agent.

One known mechanism by which certain drug and multidrug resistance modulators function is by their interaction with a protein that is variously called Multidrug-Resistance 1 protein (MDR1), Pleiotropic- glycoprotein (P-glycoprotein), Pgp, or P170, referred to herein as "P-glycoprotein". P-glycoprotein is endogenous in cell membranes, including certain drug resistant cells, multidrug resistant tumor cells, gastrointestinal tract cells, and the endothelial cells that form the blood brain barrier. P-glycoprotein acts as an efflux pump for the cell. Certain substances, undesirably including treatment drugs for various diseases, are pumped out of the cell by the P-glycoprotein prior to their having an effect on the cell. Drug and multidrug resistance modulators interact with P-glycoprotein. This interaction interferes with the P-glycoprotein "drug efflux pump" action thereby permitting the treatment drug to enter and remain in the cell and have its intended effect.

In addition to inhibiting the efflux of various drugs from tumor cells, drug and multidrug resistance modulators that interact with P-glycoprotein also function to enhance oral bioavailability of nutrients or drugs, that are affected by the action of P-glycoprotein, through the gastrointestinal tract. Oral bioavailability refers to the ability of a drug that is administered orally to be transported across the gastrointestinal tract and enter into the bloodstream. A drug or multidrug resistance modulator that interacts with P-glycoprotein should enhance the oral bioavailability of a drug or nutrient by interfering with the efflux pump action of P-glycoprotein.

P-glycoprotein is believed to be present on both sides of the endothelial cell layer of the capillary tube of the brain. It is this capillary tube that functions physiologically as the blood-brain barrier. The blood brain barrier is believed to restrict the entry of many different types of compounds, including drugs whose site of action is within the brain, from entering the brain. Certain drug and multidrug resistance modulators that interact with P-glycoprotein also can function to enhance bioavailability of a drug to the brain by interacting with P-glycoprotein and thus interfering with the drug efflux pump action of P-glycoprotein on the treatment drug. This interference permits more of the treatment drug to cross the blood-brain barrier into the brain and remain there.

Certain drug or multidrug resistance modulators that interact with P-glycoprotein are known. They include: verapamil (a calcium channel blocker that lowers blood pressure and has also been found effective in vitro for treating drug-resistant malaria), certain steroids, trifluoroperazine (a central nervous system agent), vindoline, and reserpine (an α-2 blocker with central nervous system properties).

U.S. Pat. No. 5,112,817 to Fukazawa et al. discloses certain quinoline derivatives useful for the treatment of multidrug resistance in cancer. One of the initially promising active agents, MS-073, was found to be active in in vitro testing. However, MS-073 was found to have poor oral bioavailability and to suffer from instability problems in solution. Other compounds in the series, such as the biphenylmethylcarbonyl derivative MS-209, have been found to have better stability and oral bioavailability, but require the administration of higher doses to be effective as a multidrug resistance modulator.

PCT Patent Application PCT/US94/04215 (Publication No. WO 94/24107) discloses 10,11-cyclopropyldibenzosuberane derivatives which are described as being useful as multidrug resistance modulators.

There remains a need to discover additional compounds that will interact with P-glycoprotein so that they will act as drug and multidrug resistance modulators to treat drug and multidrug resistance in various diseases. Additional compounds that interact with P-glycoprotein are also needed to act to enhance bioavailability of a drug or drugs to the brain and/or to act to enhance oral bioavailability of a drug or drugs.

SUMMARY OF THE INVENTION

The first aspect of the present invention is a compound of Formula (C):

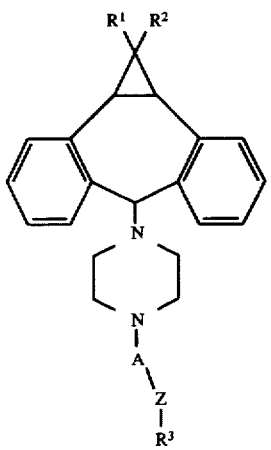

(C)

where:
R$^1$ and R$^2$ are independently hydrogen or halo;
A is —CH$_2$—CH$_2$—or —CH$_2$—CHR$^4$—(CH$_2$)$_n$—;
where n is 1 or 2;
R$^4$ is —H, —OH, or —R$^5$;

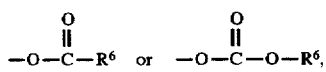

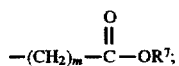

where: m is 1, 2, 3, 4, 5 or 6, and R$^7$ is —H or C$_1$–C$_6$ alkyl; providing when A is —CH$_2$—CHR$^4$—(CH$_2$)$_n$—, A and Z are oriented as —CH$_2$—CHR$^4$—(CH$_2$)$_n$—Z—;

Z is selected from the group consisting of —S—, —S(O)$_w$—, and —CH2—, where w is 1 or 2;

R$^3$ is an aryl moiety selected from the group consisting of phenyl, substituted phenyl, heteroaryl, substituted heteroaryl, polynuclear aryl and substituted polynuclear aryl;

with the proviso that Z is connected to R$^3$ at a ring carbon atom of R$^3$;

and pharmaceutically acceptable salts or solvates thereof.

The present invention also provides pharmaceutical compositions comprising a compound or salt or solvate thereof of Formula (C) in association with a pharmaceutically acceptable carrier, diluent or excipient.

The present invention further provides pharmaceutical compositions comprising a compound or salt or solvate thereof of Formula (C) and a cancer treatment drug in association with a pharmaceutically acceptable carrier, diluent or excipient.

The present invention further provides pharmaceutical compositions comprising a compound or salt or solvate thereof of Formula (C) and a malaria treatment drug in association with a pharmaceutically acceptable carrier, diluent or excipient.

The present invention further provides a method of treatment for a drug resistant disease comprising coadministering to a mammal in need thereof a resistance modulating amount of a compound or salt or solvate thereof of Formula (C) and an effective amount of a treatment drug for said drug resistant disease.

The present invention further provides a method of treatment for a multidrug resistant disease comprising coadministering to a mammal in need thereof a multidrug resistance modulating amount of a compound or salt or solvate thereof of Formula (C) and an effective amount of a treatment drug for said multidrug resistant disease.

The present invention further provides a method for enhancing bioavailability of a drug to the brain, comprising coadministering to a mammal in need thereof a therapeutically effective amount of said drug and an amount of a compound or salt or solvate thereof of Formula (C) sufficient to allow said drug to cross the blood-brain barrier and enter the brain.

The present invention further provides a method for enhancing oral bioavailability of a drug comprising administering to a mammal in need thereof a therapeutically effective amount of said drug and an amount of a compound or salt or solvate thereof of Formula (C) sufficient to allow said drug to be transported across the gastrointestinal tract and enter the bloodstream.

DETAILED DESCRIPTION OF THE INVENTION

The following definitions are set forth to illustrate and define the meaning and scope of the various terms used to describe the invention herein.

The term "alkyl" refers to a fully saturated monovalent moiety having the stated number of carbon atoms containing only carbon and hydrogen, and which may be linear or branched. This term is exemplified by moieties containing from 1 to 6 carbon atoms, such as, but not limited to, methyl, ethyl, propyl, t-butyl, pentyl, isopentyl, and hexyl. C$_1$–C$_4$ alkyl refers to alkyl groups of from 1–4 carbon atoms.

The term "alkandiyl" refers to a fully saturated linear divalent moiety containing only carbon and hydrogen and having the stated number of carbon atoms. Alkandiyls are derived from alkanes by removal of a hydrogen atom from each of the two terminal carbons in the chain. This term is exemplified by compounds containing from 1 to 6 carbon atoms, such as, but not limited to, methandiyl (a.k.a. methylene), ethan-1,2-diyl, propan-1,3-diyl, butan-1,4- diyl, pentan-1,5-diyl, and hexan-1,6-diyl. C$_1$–C$_4$ alkandiyl refers to alkandiyl groups of from 1–4 carbon atoms.

The term "-oxy(C$_1$–C$_6$ alkanoyl)" refers to the structure:

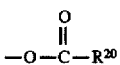

where R$^{20}$ is C$_1$–C$_6$ alkyl.

The term "-oxycarbonyl(C$_1$–C$_6$ alkanoxy)" refers to the structure:

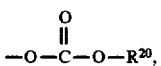

where R$^{20}$ is C$_1$–C$_6$ alkyl.

The term "11-oxycarbonyl(C$_1$–C$_6$ alkandiyl)carboxy" refers to the structure:

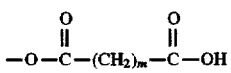

where m is 1, 2, 3, 4, 5 or 6.

The term "1-oxycarbonyl(C$_1$–C$_6$ alkandiyl)carbonyl-(C$_1$–C$_6$ alkanoxy)" refers to the structure:

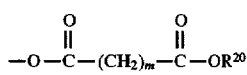

where m and $R^{20}$ are defined as above.

The term "-oxycarbonyloxy($C_1$-$C_6$ alkandiyl)- carboxy" refers to the structure:

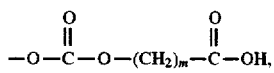

where m is defined as above.

The term "-oxycarbonyloxy($C_1$-$C_6$ alkandiyl)carbonyl-($C_1$-$C_6$ alkanoxy)" refers to the structure:

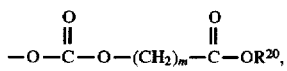

where m and $R^{20}$ are defined as above.

The term "aromatic" refers to an unsaturated planar ring containing one or more groups of atoms in a -cyclic array that contains clouds of delocalized π electrons above and below the plane of the atoms; furthermore, in each ring, the π clouds must contain a total of (4e+2) π electrons, where e is any positive integer.

The term "aryl" refers to a monovalent aromatic ring or rings. Aryl rings may optionally be substituted.

The term "heteroaromatic ring" refers to an aromatic ring containing at least three and at most five carbon atoms and at least one and at most three heteroatoms, with said heteroatom(s) being independently selected from the group consisting of nitrogen, oxygen and sulfur, providing that when there are only three carbon atoms present in the ring, there must be at least two independently selected heteroatoms in the ring. The term "heteroaryl" refers to a monovalent heteroaromatic ring. Examples of heteroaryl moieties include, but are not limited to, the following structures:

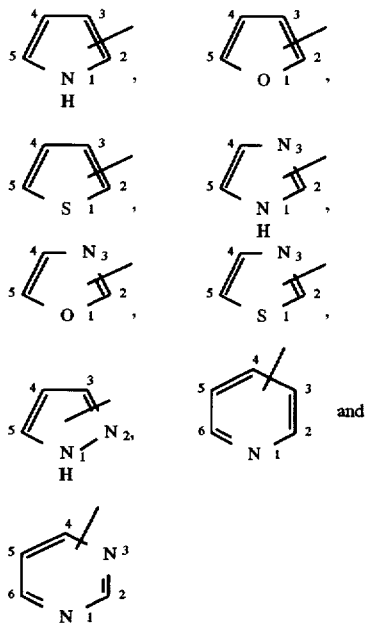

Heteroaryl rings may optionally be substituted.

Polynuclear aryl moieties are monovalent aromatic multi-ring fused structures. When the rings are all carbocyclic, these polynuclear aryl moieties contain at least two and at most four fused rings. When there is at least one heterocyclic ring, polynuclear aryl moieties contain two fused rings. Polynuclear aryl moieties include:

A) phenyl fused to at least one and at most three benzene rings;
B) heteroaryl fused to a benzene ring;
C) phenyl fused to a heteroaromatic ring; and
D) heteroaryl fused to a heteroaromatic ring.

Polynuclear aryl moieties may optionally be substituted.

Examples of "phenyl fused to at least one and at most three benzene rings" structures include, but are not limited to, the following:

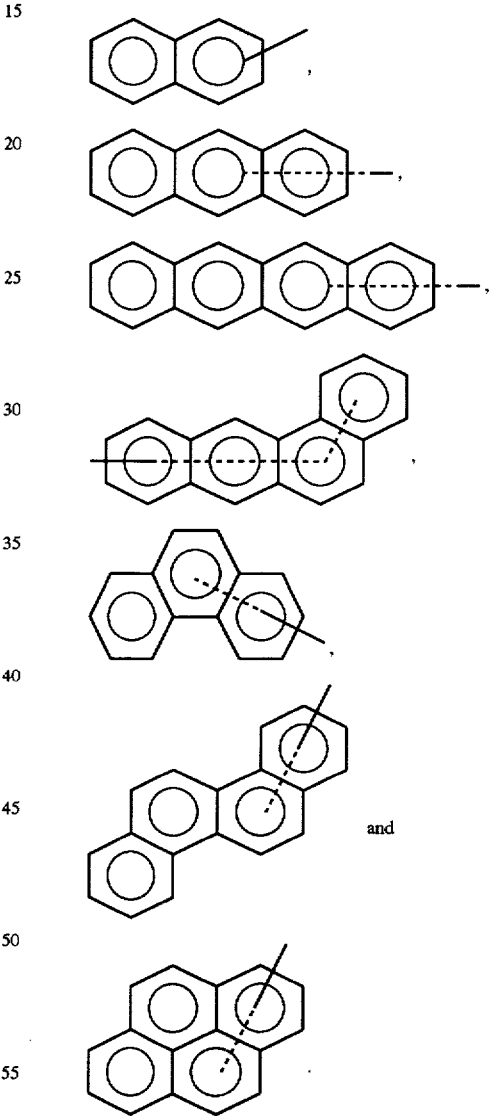

The solid bond that becomes a dotted line bond present in the above structures indicates that the bond can be attached to any available carbon in any ring that the solid-dotted line intersects. This convention will be used for these structures and all the other fused ring structures that present multiple sites for bonding.

Examples of "heteroaryl fused to a benzene ring" and "phenyl fused to a heteroaromatic ring"; structures include, but are not limited to, the following:

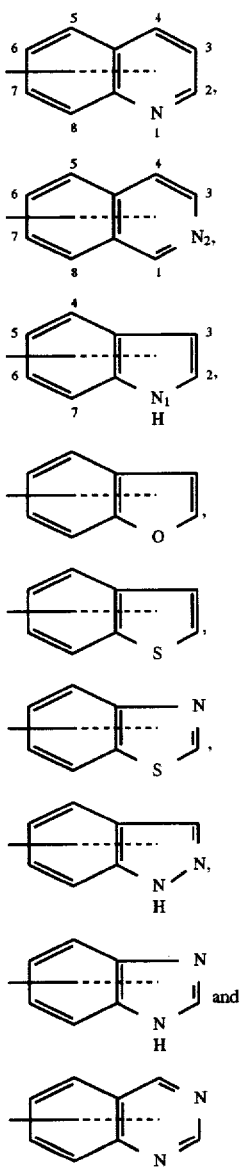

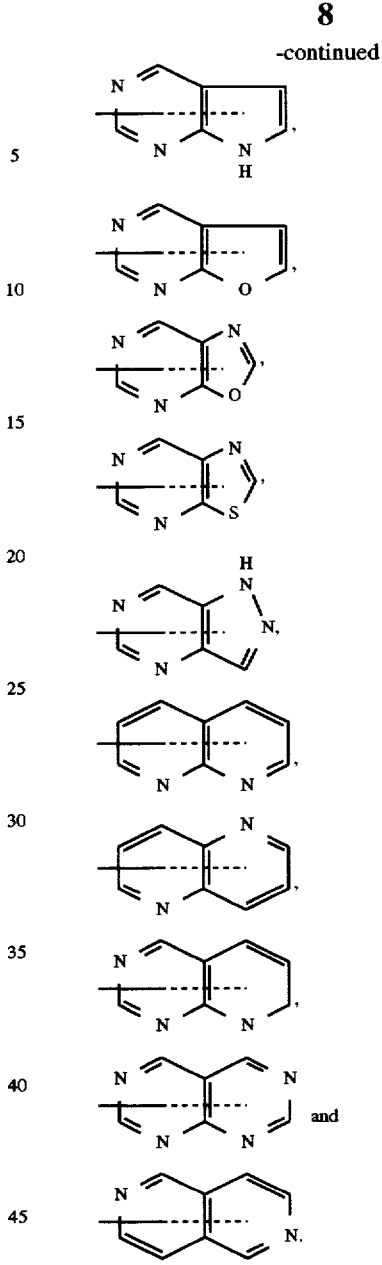

Whether the structure is "heteroaryl fused to a benzene ring" or "phenyl fused to a heteroaromatic ring", depends upon which ring of $R^3$ the bond to the Z component of Formula (C) is attached.

Examples of "heteroaryl fused to a heteroaromatic ring" structures include, but are not limited to, the following:

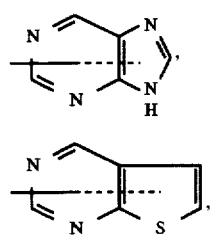

The term "substituted" means one to three hydrogens attached to carbons of the ring have been replaced with a like number of moieties independently selected from the group consisting of $C_1$–$C_4$ alkyl, bromo, chloro, fluoro, iodo, cyano, amino, nitro, trifluoromethyl, difluoromethoxy, and hydroxyl, with the proviso that any substituted structure must be so configured that it is sterically feasible, affords a stable structure and is capable of reacting as described herein.

The term "fused" refers to rings that share a pair of carbon atoms.

The term "halo" refers to fluoro, bromo, chloro and iodo.

The term "optional" in reference to a substituent, means that the substituent may or may not be present where indicated.

A "pharmaceutically acceptable salt" may be any non-toxic salt derived from an inorganic or organic acid that is suitable for administration as a drug. The salts are derived from inorganic acids, such as hydrochloric acid, hydrobromic acid, sulfuric acid (giving the sulfate and bisulfate as acidic salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxybenzoyl) benzoic acid, 1, 2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methylbicyclo[2.2.2]oct-2-ene-1-carboxylic acid, glucoheptonic acid, 4,4'-methylenebis(3-hydroxy-2- naphthoic) acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

A "pharmaceutically acceptable solvate" refers to an aggregate of a compound of Formula (C) with solvent molecules. The solvent may be water or any common organic solvent.

The term "bioavailability" refers to the degree and rate at which a drug, or other substance, becomes available to a target tissue within a mammal.

The term "treatment" or "treating" means administering an appropriate therapeutic or prophylactic amount of a compound to a mammal.

The term "effective amount" means a dosage sufficient to cause a positive change in the disease state being treated. The term "positive change" will vary in meaning depending on the patient, the disease and the treatment being undergone but is readily determined by one of ordinary skill in the art. For example, an effective amount of an oncolytic can be an amount that causes a reduction in the size of a cancerous tumor, or where no reduction in tumor size occurs, an effective amount of an oncolytic could be that amount that causes a decrease in analgesic consumption for the patient suffering from cancer.

The term "coadministering" means a disease treatment drug and a compound of Formula (C) are given to a mammal. The drug and the compound of Formula (C) are given to a mammal simultaneously or at different times.

The term "drug resistance" refers to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously responded to. "Multidrug resistance" means a specific type of drug resistance characterized by cross-resistance of a disease to more than one functionally and/or structurally unrelated drugs. Multidrug resistance can be either intrinsic or acquired.

For the compounds of Formula (C), preferred moieties for the variable substituents are as follows:

$R^1$ and $R^2$: both halo, more preferred that both are fluoro;

$R^3$: quinolyl, substituted quinolyl, isoquinolyl, substituted isoquinolyl, indolinyl, substituted indolinyl, naphthyl and substituted naphthyl;

A: —$CH_2$—$CHR^4$—$(CH_2)_n$—, where $R^4$ is preferably —OH and n is 1 or 2;

Z: —S— or —$CH_2$—.

The compounds of Formula (C) exist in two isomeric configurations defined by the relationship of the 10,11-cyclopropyl and the 5-piperazinyl substituents on the dibenzosuberane.

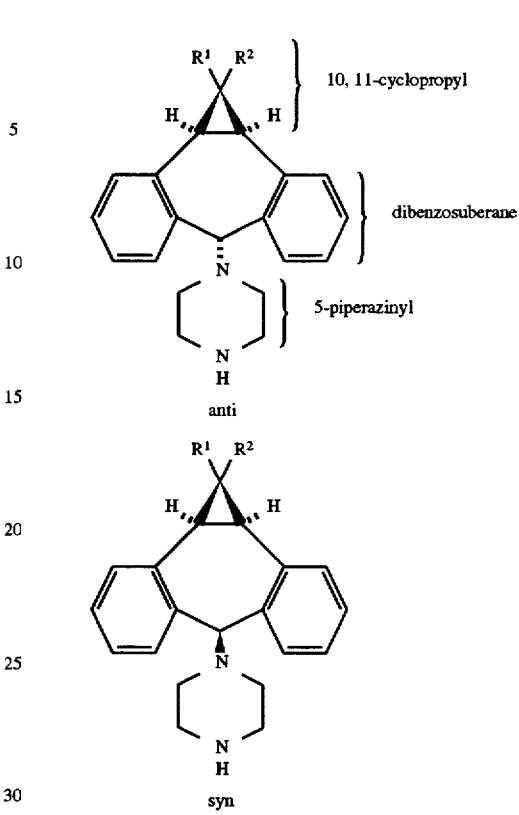

When the 10,11-cyclopropyl and the 5-piperazinyl substituents are both oriented in the same direction with respect to the dibenzosuberane (e.g. both up or both down) the isomeric form is called "syn." When the 10,11- cyclopropyl and the 5-piperazinyl substituents are oriented in opposite directions with respect to the dibenzosuberane (e.g., one up and the other down) the isomeric form is called "anti." In general, the drug/multidrug resistance activity of the compounds of Formula (C) in the "anti" configuration has been found to be far superior to the activity of the compounds of Formula (C) in the "syn" configuration.

Certain compounds of Formula (C) will have an asymmetric center within the "A" component when $R^4$ is not hydrogen. These compounds can exist in two stereochemical forms, called (R)— and (S)—, or as mixtures of the two stereoisomers.

While specific stereoisomers are disclosed and named, the present invention is to be interpreted to include both the "anti" and "syn" configurations, the individual (R)— and (S)— stereoisomers within those configurations, as well as mixtures, racemic and otherwise, thereof. Accordingly the designation (syn, anti)- in a name means that both individual stereoisomers are included in the description of the preferred compound. Similarly, the designation (R,S) means that both individual stereoisomers at the indicated position are included in the description of the preferred compound.

Preferred compounds of the claimed invention include:

1a) (syn, anti)-5-{1-(4-(10,11-difluorocyclopropyldibenzosuber-5-yl)piperazin-1-yl)prop-3-yl}quinoline, or a pharmaceutically acceptable salt or solvate thereof;

1b) (syn, anti)-5-{1-(4-(10,11-difluorocyclopropyldibenzosuber-5-yl)piperazin-1-yl)but-4-yl}quinoline, or a pharmaceutically acceptable salt or solvate thereof;

1c) (syn, anti)-5-{1-(4-(10,11-difluorocyclopropyldibenzosuber-5-yl)piperazin-1-yl)pent-5-yl}quinoline, or a pharmaceutically acceptable salt or solvate thereof;

1d) (syn, anti)-5-{1-(4-(10,11-difluorocyclopropyldibenzosuber-5-yl)piperazin-1-yl)eth-2-ylthio}quinoline, or a pharmaceutically acceptable salt or solvate thereof;

1e) (syn, anti)-5-(1-(4-(10,11-difluorocyclopropyldibenzosuber-5-yl)piperazin-1-yl)prop-3-ylthio}quinoline, or a pharmaceutically acceptable salt or solvate thereof;

1f) (syn, anti)-5-{1-(4-(10,11-difluorocyclopropyldibenzosuber-5-yl)piperazin-1-yl)but-4-ylthio}quinoline, or a pharmaceutically acceptable salt or solvate thereof;

1g) (syn, anti)-5-{1-(4-(10,11-difluorocyclopropyldibenzosuber-5-yl)piperazin-1-yl)eth-2-ylsulfinyl}quinoline, or a pharmaceutically acceptable salt or solvate thereof;

1h) (syn, anti)-5-{1-(4-(10,11-difluorocyclopropyldibenzosuber-5-yl)piperazin-1-yl)prop-3-ylsulfinyl}quinoline, or a pharmaceutically acceptable salt or solvate thereof;

1i) (syn, anti)-5-{1-(4-(10,11-difluorocyclopropyldibenzosuber-5-yl)piperazin-1-yl)but-4-ylsulfinyl}quinoline, or a pharmaceutically acceptable salt or solvate thereof;

1j) (syn, anti)-5-{1-(4-(10,11-difluorocyclopropyldibenzosuber-5-yl)piperazin-1-yl)eth-2-ylsulfonyl}quinoline, or a pharmaceutically acceptable salt or solvate thereof;

1k) (syn, anti)-5-(1-(4-(10,11-difluorocyclopropyldibenzosuber-5-yl)piperazin-1-yl)prop-3-ylsulfonyl}quinoline, or a pharmaceutically acceptable salt or solvate thereof;

1l) (syn, anti)-5-fl-(4-(10,11-difluorocyclopropyldibenzosuber-5-yl)piperazin-1-yl)but-4-ylsulfonyl}quinoline, or a pharmaceutically acceptable salt or solvate thereof;

1m) (syn, anti)-5-{1-(4-(10,11-difluorocyclopropyldibenzosuber-5-yl)piperazin-1-yl)-2(R,S)-hydroxybut-4-yl}quinoline, or a pharmaceutically acceptable salt or solvate thereof;

1n) (syn, anti)-5-{1-(4-(10,11-difluorocyclopropyldibenzosuber-5-yl)piperazin-1-yl)-2(R,S)-hydroxypent-5-yl}quinoline, or a pharmaceutically acceptable salt or solvate thereof;

1o) (syn, anti)-5-{1-(4-(10,11-difluorocyclopropyldibenzosuber-5-yl)piperazin-1-yl)-2(R,S)-hydroxyprop-3-ylthio}- quinoline, or a pharmaceutically acceptable salt or solvate thereof;

1p) (syn, anti)-5-tl-(4-(10,11-difluorocyclopropyldibenzosuber-5-yl)piperazin-1-yl)-2(R,S)-hydroxybut-4-ylthio}quinoline, or a pharmaceutically acceptable salt or solvate thereof;

1q) (syn, anti)-5-{1-(4-(10,11-difluorocyclopropyldibenzosuber-5-yl)piperazin-1-yl)-2(R,S)-hydroxyprop-3-ylsulfinyl}quinoline, or a pharmaceutically acceptable salt or solvate thereof;

1r) (syn, anti)-5-(i-(4-(10,11-difluorocyclopropyldibenzosuber-5-yl)piperazin-1-yl)-2(R,S)-hydroxybut-4-ylsulfinyl}quinoline, or a pharmaceutically acceptable salt or solvate thereof;

1s) (syn, anti)-5-{1-(4-(10,11-difluorocyclopropyldibenzosuber-5-yl)piperazin-1-yl)-2(R,S)-hydroxyprop-3-ylsulfonyl}-quinoline, or a pharmaceutically acceptable salt or solvate thereof;

1t) (syn, anti)-5-{1-(4-(10,11-difluorocyclopropyldibenzosuber-5-yl)piperazin-1-yl)-2(R,S)-hydroxybut-4-ylsulfonyl}- quinoline, or a pharmaceutically acceptable salt or solvate thereof;

1u) (syn, anti)-5-{1-(4-(10,11-difluorocyclopropyldibenzosuber-5-yl)piperazin-1-yl)-2(R,S)-oxy($C_1$–$C_6$ alkanoyl)but-4- yl}quinoline, or a pharmaceutically acceptable salt or solvate thereof;

1v) (syn, anti)-5-{1-(4-(10,11-difluorocyclopropyldibenzosuber-5-yl)piperazin-1-yl)-2(R,S)-oxy($C_1$–$C_6$ alkanoyl)pent- 5-yl}quinoline, or a pharmaceutically acceptable salt or solvate thereof;

1w) (syn, anti)-5-{1-(4-(10,11-difluorocyclopropyldibenzosuber-5-yl)piperazin-1-yl)-2(R,S)-oxycarbonyl($C_1$–$C_6$ alkanoxy)but-4-yl)quinoline, or a pharmaceutically acceptable salt or solvate thereof;

1x) (syn, anti)-5-{1-(4-(10,11-difluorocyclopropyldibenzosuber-5-yl)piperazin-1-yl)-2(R,S)-oxycarbonyl($C_1$–$C_6$ alkanoxy)pent-5-yl}quinoline, or a pharmaceutically acceptable salt or solvate thereof;

1y) (syn, anti)-5-{1-(4-(10,11-difluorocyclopropyldibenzosuber-5-yl)piperazin-1-yl)-2(R,S)-oxycarbonyloxy ($C_1$–$C_6$ alkandiyl)carbonyl($C_1$–$C_6$ alkanoxy)but-4-ylyquinoline, or a pharmaceutically acceptable salt or solvate thereof;

1z) (syn, anti)-5-{1-(4-(10,11-difluorocyclopropyldibenzosuber-5-yl)piperazin-1-yl)-2(R,S)-oxycarbonyloxy ($C_1$–$C_6$ alkandiyl)carbonyl($C_1$–$C_6$ alkanoxy)pent-5-yl}quinoline, or a pharmaceutically acceptable salt or solvate thereof;

1aa) (syn, anti)-5-{1-(4-(10,11-difluorocyclopropyldibenzosuber-5-yl)piperazin-1-yl)-2(R,S)-oxycarbonyloxy ($C_1$–$C_6$ alkandiyl)carboxybut-4-yl}quinoline, or a pharmaceutically acceptable salt or solvate thereof;

1bb) (syn, anti)-5-{1-(4-(10,11-difluorocyclopropyldibenzosuber-5-yl)piperazin-1-yl)-2(R,S)-oxycarbonyloxy ($C_1$–$C_6$ alkandiyl)carboxypent-5-yl}quinoline, or a pharmaceutically acceptable salt or solvate thereof;

1cc) (syn, anti)-5-{1-(4-(10,11-difluorocyclopropyldibenzosuber-5-yl)piperazin-1-yl)-2(R,S)-oxycarbonyl($C_1$–$C_6$ alkandiyl)carboxybut-4-yl}quinoline, or a pharmaceutically acceptable salt or solvate thereof;

1dd) (syn, anti)-5-{1-(4-(10,11-difluorocyclopropyldibenzosuber-5-yl)piperazin-1-yl)-2(R,S)-oxycarbonyl($C_1$–$C_6$ alkandiyl)carbonyl($C_1$–$C_6$ alkanoxy)pent-5-yl)quinoline, or a pharmaceutically acceptable salt or solvate thereof;

2a) (syn, anti)-5-{1-(4-(10,11-difluorocyclopropyldibenzosuber-5-yl)piperazin-1-yl)prop-3-yl}isoquinoline, or a pharmaceutically acceptable salt or solvate thereof;

2b) (syn, anti)-5-{1-(4-(10,11-difluorocyclopropyldibenzosuber-5-yl)piperazin-1-yl)but-4-yl}isoquinoline, or a pharmaceutically acceptable salt or solvate thereof;

2c) (syn, anti)-5-{1-(4-(10,11-difluorocyclopropyldibenzosuber-5-yl)piperazin-1-yl)pent-5-yl}isoquinoline, or a pharmaceutically acceptable salt or solvate thereof;

2d) (syn, anti)-5-{1-(4-(10,11-difluorocyclopropyldibenzosuber-5-yl)piperazin-1-yl)eth-2-ylthio}isoquinoline, or a pharmaceutically acceptable salt or solvate thereof;

2e) (syn, anti)-5-{1-(4-(10,11-difluorocyclopropyldibenzosuber-5-yl)piperazin-1-yl)prop-3-ylthioyisoquinoline, or a pharmaceutically acceptable salt or solvate thereof;

2f) (syn, anti)-5-{1-(4-(10,11-difluorocyclopropyldibenzosuber-5-yl)piperazin-1-yl)but-4-ylthio}isoquinoline, or a pharmaceutically acceptable salt or solvate thereof;

2g) (syn, anti)-5-{1-(4-(10,11-difluorocyclopropyldibenzosuber-5-yl)piperazin-1-yl)eth-2-ylsulfinyl}isoquinoline, or a pharmaceutically acceptable salt or solvate thereof;

2h) (syn, anti)-5-{1-(4-(10,11-difluorocyclopropyldibenzosuber-5-yl)piperazin-1-yl)prop-3-ylsulfinyl}isoquinoline, or a pharmaceutically acceptable salt or solvate thereof;

2i) (syn, anti)-5-{1-(4-(10,11-difluorocyclopropyldibenzosuber-$^5$-yl)piperazin-1-yl)but-4-ylsulfinyl}isoquinoline, or a pharmaceutically acceptable salt or solvate thereof;

2j) (syn, anti)-5-{1-(4-(10,11-difluorocyclopropyldibenzosuber-5-yl)piperazin-1-yl)eth-2-ylsulfonyl}isoquinoline, or a pharmaceutically acceptable salt or solvate thereof;

2k) (syn, anti)-5-{1-(4-(10,11-difluorocyclopropyldibenzosuber-5-yl)piperazin-1-yl)prop-3-

2l) (syn, anti)-5-{1-(4-(10,11-difluorocyclopropyldibenzo-suber-5-yl)piperazin-1-yl)but-4-ylsulfonyl}isoquinoline, or a pharmaceutically acceptable salt or solvate thereof;

2m) (syn, anti)-5-{1-(4-(10,11-difluorocyclopropyldibenzo-suber-5-yl)piperazin-1-yl)-2(R,S)-hydroxybut-4-yl}isoquinoline, or a pharmaceutically acceptable salt or solvate thereof;

2n) (syn, anti)-5-{1-(4-(10,11-difluorocyclopropyldibenzo-suber-5-yl)piperazin-1-yl)-2(R,S)-hydroxypent-5-yl}isoquinoline, or a pharmaceutically acceptable salt or solvate thereof;

2o) (syn, anti)-5-{1-(4-(10,11-difluorocyclopropyldibenzo-suber-5-yl)piperazin-1-yl)-2(R,S)-hydroxyprop-3-ylthio}isoquinoline, or a pharmaceutically acceptable salt or solvate thereof;

2p) (syn, anti)-5-{1-(4-(10,11-difluorocyclopropyldibenzo-suber-5-yl)piperazin-1-yl)-2(R,S)-hydroxybut-4-ylthio}isoquinoline, or a pharmaceutically acceptable salt or solvate thereof;

2q) (syn, anti)-5-{1-($^4$-(10,11-difluorocyclopropyldibenzo-suber-5-yl)piperazin-1-yl)-2(R,S)-hydroxyprop-3-ylsulfinyl}-isoquinoline, or a pharmaceutically acceptable salt or solvate thereof;

2r) (syn, anti)-$^5$-{1-(4-(10,11-difluorocyclopropyldibenzo-suber-5-yl)piperazin-1-yl)-2(R,S)-hydroxybut-4-ylsulfinyl}isoquinoline, or a pharmaceutically acceptable salt or solvate thereof;

2s) (syn, anti)-$^5$-{1-($^4$-(10,11-difluorocyclopropyldibenzo-suber-5-yl)piperazin-1-yl)-2(R,S)-hydroxyprop-3-ylsulfonyl}isoquinoline, or a pharmaceutically acceptable salt or solvate thereof;

2t) (syn, anti)-5-{1-(4-(10,11-difluorocyclopropyldibenzo-suber-5-yl)piperazin-1-yl)-2(R,S)-hydroxybut-4-ylsulfonyl}isoquinoline, or a pharmaceutically acceptable salt or solvate thereof;

2u) (syn, anti)-5-{1-(4-(10,11-difluorocyclopropyldibenzo-suber-5-yl)piperazin-1-yl)-2(R,S)-oxy($C_1$–$C_6$ alkanoyl)but-4- yl}isoquinoline, or a pharmaceutically acceptable salt or solvate thereof;

2v) (syn, anti)-5-{1-(4-(10,11-difluorocyclopropyldibenzo-suber-5-yl)piperazin-1-yl)-2(R,S)-oxy($C_1$–$C_6$ alkanoyl)pent- 5-yl}isoquinoline, or a pharmaceutically acceptable salt or solvate thereof;

2w) (syn, anti)-5-{1-(4-(10,11-difluorocyclopropyldibenzo-suber-5-yl)piperazin-1-yl)-2(R,S)-oxycarbonyl($C_1$–$C_6$ alkanoxy)but-4-ylyisoquinoline, or a pharmaceutically acceptable salt or solvate thereof;

2x) (syn, anti)-5-{1-(4-(10,11-difluorocyclopropyldibenzo-suber-5-yl)piperazin-1-yl)-2(R,S)-oxycarbonyl($C_1$–$C_6$ alkanoxy)pent-5-ylisoquinoline, or a pharmaceutically acceptable salt or solvate thereof;

2y) (syn, anti)-5-{1-(4-(10,11-difluorocyclopropyldibenzo-suber-5-yl)piperazin-1-yl)-2(R,S)-oxycarbonyloxy ($C_1$–$C_6$ alkandiyl)carbonyl($C_1$–$C_6$ alkanoxy)but-4-yllisoquinoline, or a pharmaceutically acceptable salt or solvate thereof;

2z) (syn, anti)-5-{1-(4-(10,11-difluorocyclopropyldibenzo-suber-5-yl)piperazin-1-yl)-2(R,S)-oxycarbonyloxy ($C_1$–$C_6$ alkandiyl)carbonyl($C_1$–$C_6$ alkanoxy)pent-5-ylyisoquinoline, or a pharmaceutically acceptable salt or solvate thereof;

2aa) (syn, anti)-5-{1-(4-(10,11-difluorocyclopropyldibenzo-suber-5-yl)piperazin-1-yl)-2(R,S)-oxycarbonyloxy ($C_1$–$C_6$ alkandiyl)carboxybut-4-yl}isoquinoline, or a pharmaceutically acceptable salt or solvate thereof;

2bb) (syn, anti)-5-{1-(4-(10,11-difluorocyclopropyldibenzo-suber-5-yl)piperazin-1-yl)-2(R,S)-oxycarbonyloxy ($C_1$–$C_6$ alkandiyl)carboxypent-5-yl}isoquinoline, or a pharmaceutically acceptable salt or solvate thereof;

2cc) (syn, anti)-5-{1-(4-(10,11-difluorocyclopropyldibenzo-suber-5-yl)piperazin-1-yl)-2(R,S)-oxycarbonyl($C_1$–$C_6$ alkandiyl)carboxybut-4-yl}isoquinoline, or a pharmaceutically acceptable salt or solvate thereof;

2dd) (syn, anti)-5-{1-(4-(10,11-difluorocyclopropyldibenzo-suber-5-yl)piperazin-1-yl)-2(R,S)-oxycarbonyl($C_1$–$C_6$ alkandiyl)carbonyl($C_1$–$C_6$ alkanoxy)pent-5-ylyisoquinoline, or a pharmaceutically acceptable salt or solvate thereof;

3a) (syn, anti)-4-{1-(4-(10,11-difluorocyclopropyldibenzo-suber-5-yl)piperazin-1-yl)prop-3-yl}indole, or a pharmaceutically acceptable salt or solvate thereof;

3b) (syn, anti)-4-{1-(4-(10,11-difluorocyclopropyldibenzo-suber-5-yl)piperazin-1-yl)but-4-yl}indole, or a pharmaceutically acceptable salt or solvate thereof;

3c) (syn, anti)-$^4$-{1-($^4$-(10,11-difluorocyclopropyldibenzo-suber-5-yl)piperazin-1-yl)pent-5-yl}indole, or a pharmaceutically acceptable salt or solvate thereof;

3d) (syn, anti)-$^4$-{$^1$-($^4$-(10,11-difluorocyclopropyldibenzo-suber-5-yl)piperazin-1-yl)eth-2-ylthio}indole, or a pharmaceutically acceptable salt or solvate thereof;

3e) (syn, anti)-$^4$-{1-(4-(10,11-difluorocyclopropyldibenzo-suber-5-yl)piperazin-1-yl)prop-3-ylthio}indole, or a pharmaceutically acceptable salt or solvate thereof;

3f) (syn, anti)-4-{1-(4-(10,11-difluorocyclopropyldibenzo-suber-5-yl)piperazin-1-yl)but-4-ylthio}indole, or a pharmaceutically acceptable salt or solvate thereof;

3g) (syn, anti)-$^4$-{1-(4-(10,11-difluorocyclopropyldibenzo-suber-5-yl)piperazin-1-yl)eth-2-ylsulfinyl}indole, or a pharmaceutically acceptable salt or solvate thereof;

3h) (syn, anti)-4-{1-(4-(10,11-difluorocyclopropyldibenzo-suber-5-yl)piperazin-1-yl)prop-3-ylsulfinyl}indole, or a pharmaceutically acceptable salt or solvate thereof;

3i) (syn, anti)-4-{1-(4-(10,11-difluorocyclopropyldibenzo-suber-5-yl)piperazin-1-yl)but-4-ylsulfinylindole, or a pharmaceutically acceptable salt or solvate thereof;

3j) (syn, anti)-4-{1-(4-(10,11-difluorocyclopropyldibenzo-suber-5-yl)piperazin-1-yl)eth-2-ylsulfonyl}indole, or a pharmaceutically acceptable salt or solvate thereof;

3k) (syn, anti)-$^4$-{1-(4-(10,11-difluorocyclopropyldibenzo-suber-5-yl)piperazin-1-yl)prop-3-ylsulfonyl}indole, or a pharmaceutically acceptable salt or solvate thereof;

3l) (syn, anti)-4-{1-(4-(10,11-difluorocyclopropyldibenzo-suber-5-yl)piperazin-1-yl)but-4-ylsulfonyl}indole, or a pharmaceutically acceptable salt or solvate thereof;

3m) (syn, anti)-4-{1-(4-(10,11-difluorocyclopropyldibenzo-suber-5-yl)piperazin-1-yl)-2(R,S)-hydroxybut-4-yl}indole, or a pharmaceutically acceptable salt or solvate thereof;

3n) (syn, anti)-4-{1-(4-(10,11-difluorocyclopropyldibenzo-suber-5-yl)piperazin-1-yl)-2(R,S)-hydroxypent-5-yl}indole, or a pharmaceutically acceptable salt or solvate thereof;

3o) (syn, anti)-4-{1-(4-(10,11-difluorocyclopropyldibenzo-suber-5-yl)piperazin-1-yl)-2(R,S)-hydroxyprop-3-ylthio}indole, or a pharmaceutically acceptable salt or solvate thereof;

3p) (syn, anti)-4-{1-(4-(10,11-difluorocyclopropyldibenzo-suber-5-yl)piperazin-1-yl)-2(R,S)-hydroxybut-4-ylthio}indole, or a pharmaceutically acceptable salt or solvate thereof;

3q) (syn, anti)-4-{1-(4-(10,11-difluorocyclopropyldibenzo-suber-5-yl)piperazin-1-yl)-2(R,S)-hydroxyprop-3-

3r) (syn, anti)-4-{1-(4-(10,11-difluorocyclopropyldibenzo-suber-5-yl)piperazin-1-yl)-2(R,S)-hydroxybut-4-ylsulfinyl}indole, or a pharmaceutically acceptable salt or solvate thereof;

3s) (syn, anti)-4-{1-(4-(10,11-difluorocyclopropyldibenzo-suber-5-yl)piperazin-1-yl)-2(R,S)-hydroxyprop-3-ylsulfonyl}indole, or a pharmaceutically acceptable salt or solvate thereof;

3t) (syn, anti)-4-{1-(4-(10,11-difluorocyclopropyldibenzo-suber-5-yl)piperazin-1-yl)-2(R,S)-hydroxybut-4-ylsulfonyl}indole, or a pharmaceutically acceptable salt or solvate thereof;

3u) (syn, anti)-4-{1-(4-(10,11-difluorocyclopropyldibenzo-suber-5-yl)piperazin-1-yl)-2(R,S)-oxy($C_1$–$C_6$ alkanoyl)but-4-yl}indole, or a pharmaceutically acceptable salt or solvate thereof;

3v) (syn, anti)-4-{1-(4-(10,11-difluorocyclopropyldibenzo-suber-5-yl)piperazin-1-yl)-2(R,S)-oxy($C_1$–$C_6$ alkanoyl)pent-5-yl}indole, or a pharmaceutically acceptable salt or solvate thereof;

3w) (syn, anti)-4-{1-(4-(10,11-difluorocyclopropyldibenzo-suber-5-yl)piperazin-1-yl)-2(R,S)-oxycarbonyl($C_1$–$C_6$ alkanoxy)but-4-yl}indole, or a pharmaceutically acceptable salt or solvate thereof;

3x) (syn, anti)-4-{1-(4-(10,11-difluorocyclopropyldibenzo-suber-5-yl)piperazin-1-yl)-2(R,S)-oxycarbonyl($C_1$–$C_6$ alkanoxy)pent-5-yl}indole, or a pharmaceutically acceptable salt or solvate thereof;

3y) (syn, anti)-4-{1-(4-(10,11-difluorocyclopropyldibenzo-suber-5-yl)piperazin-1-yl)-2(R,S)-oxycarbonyloxy($C_1$–$C_6$ alkandiyl)carbonyl($C_1$–$C_6$ alkanoxy)but-4-yl}indole, or a pharmaceutically acceptable salt or solvate thereof;

3z) (syn, anti)-4-{1-(4-(10,11-difluorocyclopropyldibenzo-suber-5-yl)piperazin-1-yl)-2(R,S)-oxycarbonyloxy($C_1$–$C_6$ alkandiyl)carbonyl($C_1$–$C_6$ alkanoxy)pent-5-yl}indole, or a pharmaceutically acceptable salt or solvate thereof;

3aa) (syn, anti)-4-{1-(4-(10,11-difluorocyclopropyldibenzo-suber-5-yl)piperazin-1-yl)-2(R,S)-oxycarbonyloxy($C_1$–$C_6$ alkandiyl)carboxybut-4-yl}indole, or a pharmaceutically acceptable salt or solvate thereof;

3bb) (syn, anti)-4-{1-(4-(10,11-difluorocyclopropyldibenzo-suber-5-yl)piperazin-1-yl)-2(R,S)-oxycarbonyloxy($C_1$–$C_6$ alkandiyl)carboxypent-5-yl}indole, or a pharmaceutically acceptable salt or solvate thereof;

3cc) (syn, anti)-4-{1-(4-(10,11-difluorocyclopropyldibenzo-suber-5-yl)piperazin-1-yl)-2(R,S)-oxycarbonyl($C_1$–$C_6$ alkandiyl)carboxybut-4-yl}indole, or a pharmaceutically acceptable salt or solvate thereof;

3dd) (syn, anti)-4-{1-(4-(10,11-difluorocyclopropyldibenzo-suber-5-yl)piperazin-1-yl)-2(R,S)-oxycarbonyl($C_1$–$C_6$ alkandiyl)carbonyl($C_1$–$C_6$ alkanoxy)pent-5-yl}indole, or a pharmaceutically acceptable salt or solvate thereof;

4a) (syn, anti)-1-{1-(4-(10,11-difluorocyclopropyldibenzo-suber-5-yl)piperazin-1-yl)prop-3-yl}naphthalene, or a pharmaceutically acceptable salt or solvate thereof;

4b) (syn, anti)-1-{1-(4-(10,11-difluorocyclopropyldibenzo-suber-5-yl)piperazin-1-yl)but-4-yl}naphthalene, or a pharmaceutically acceptable salt or solvate thereof;

4c) (syn, anti)-1-{1-(4-(10,11-difluorocyclopropyldibenzo-suber-5-yl)piperazin-1-yl)pent-5-yl}naphthalene, or a pharmaceutically acceptable salt or solvate thereof;

4d) (syn, anti)-1-{1-(4-(10,11-difluorocyclopropyldibenzo-suber-5-yl)piperazin-1-yl)eth-2-ylthiolnaphthalene, or a pharmaceutically acceptable salt or solvate thereof;

4e) (syn, anti)-1-{1-(4-(10,11-difluorocyclopropyldibenzo-suber-5-yl)piperazin-1-yl)prop-3-ylthio}naphthalene, or a pharmaceutically acceptable salt or solvate thereof;

4f) (syn, anti)-1-{1-(4-(10,11-difluorocyclopropyldibenzo-suber-5-yl)piperazin-1-yl)but-4-ylthio}naphthalene, or a pharmaceutically acceptable salt or solvate thereof;

4g) (syn, anti)-l-{1-(4-(10,11-difluorocyclopropyldibenzo-suber-5-yl)piperazin-1-yl)eth-2-ylsulfinyl}naphthalene, or a pharmaceutically acceptable salt or solvate thereof;

4h) (syn, anti)-l-{1-($^4$-(10,11-difluorocyclopropyldibenzo-suber-5-yl)piperazin-1-yl)prop-3-ylsulfinyl}naphthalene, or a pharmaceutically acceptable salt or solvate thereof;

4i) (syn, anti)-l-{1-(4-(10,11-difluorocyclopropyldibenzo-suber-5-yl)piperazin-1-yl)but-4-ylsulfinyl)naphthalene, or a pharmaceutically acceptable salt or solvate thereof;

4j) (syn, anti)-l-{1-(4-(10,11-difluorocyclopropyldibenzo-suber-5-yl)piperazin-1-yl)eth-2-ylsulfonyl}naphthalene, or a pharmaceutically acceptable salt or solvate thereof;

4k) (syn, anti)-l-{1-(4-(10,11-difluorocyclopropyldibenzo-suber-5-yl)piperazin-1-yl)prop-3-ylsulfonylYnaphthalene, or a pharmaceutically acceptable salt or solvate thereof;

4l) (syn, anti)-l-{1-(4-(10,11-difluorocyclopropyldibenzo-suber-5-yl)piperazin-1-yl)but-4-ylsulfonyl}naphthalene, or a pharmaceutically acceptable salt or solvate thereof;

4m) (syn, anti)-1-{1-(4-(10,11-difluorocyclopropyldibenzo-suber-5-yl)piperazin-1-yl)-2(R,S)-hydroxybut-4-yl}naphthalene, or a pharmaceutically acceptable salt or solvate thereof;

4n) (syn, anti)-l-{1-(4-(10,11-difluorocyclopropyldibenzo-suber-5-yl)piperazin-1-yl)-2(R,S)-hydroxypent-5-yl}naphthalene, or a pharmaceutically acceptable salt or solvate thereof;

4o) (syn, anti)-l-{1-(4-(10,11-difluorocyclopropyldibenzo-suber-5-yl)piperazin-1-yl)-2(R,S)-hydroxyprop-3-ylthio}naphthalene, or a pharmaceutically acceptable salt or solvate thereof;

4p) (syn, anti)-l-{1-(4-(10,11-difluorocyclopropyldibenzo-suber-5-yl)piperazin-1-yl)-2(R,S)-hydroxybut-4-ylthio}naphthalene, or a pharmaceutically acceptable salt or solvate thereof;

4q) (syn, anti)-l-{1-(4-(10,11-difluorocyclopropyldibenzo-suber-5-yl)piperazin-1-yl)-2(R,S)-hydroxyprop-3-ylsulfinyl}naphthalene, or a pharmaceutically acceptable salt or solvate thereof;

4r) (syn, anti)-l-(1-(4-(10,11-difluorocyclopropyldibenzo-suber-5-yl)piperazin-1-yl)-2(R,S)-hydroxybut-4-ylsulfinyl}naphthalene, or a pharmaceutically acceptable salt or solvate thereof;

4s) (syn, anti)-1-{1-(4-(10,11-difluorocyclopropyldibenzo-suber-5-yl)piperazin-1-yl)-2(R,S)-hydroxyprop-3-ylsulfonyl}naphthalene, or a pharmaceutically acceptable salt or solvate thereof;

4t) (syn, anti)-1-{1-(4-(10,11-difluorocyclopropyldibenzo-suber-5-yl)piperazin-1-yl)-2(R,S)-hydroxybut-4-ylsulfonyl}- naphthalene, or a pharmaceutically acceptable salt or solvate thereof;

4u) (syn, anti)-1-{1-(4-(10,11-difluorocyclopropyldibenzo-suber-5-yl)piperazin-1-yl)-2(R,S)-oxy($C_1$–$C_6$ alkanoyl)but-4-yl}naphthalene, or a pharmaceutically acceptable salt or solvate thereof;

4v) (syn, anti)-1-{1-(4-(10,11-difluorocyclopropyldibenzo-suber-5-yl)piperazin-1-yl)-2(R,S)-oxy($C_1$–$C_6$ alkanoyl)pent-5-yl}naphthalene, or a pharmaceutically acceptable salt or solvate thereof;

4w) (syn, anti)-1-{1-(4-(10,11-difluorocyclopropyldibenzo-suber-5-yl)piperazin-1-yl)-2(R,S)-oxycarbonyl($C_1$–$C_6$ alkanoxy)but-4-yl}naphthalene, or a pharmaceutically acceptable salt or solvate thereof;

4x) (syn, anti)-1-{1-(4-(10,11-difluorocyclopropyldibenzo-suber-5-yl)piperazin-1-yl)-2(R,S)-oxycarbonyl(C$_1$–C$_6$ alkanoxy)pent-5-yl}naphthalene, or a pharmaceutically acceptable salt or solvate thereof;

4y) (syn, anti)-1-{1-(4-(10,11-difluorocyclopropyldibenzo-suber-5-yl)piperazin-1-yl)-2(R,S)-oxycarbonyloxy (C$_1$–C$_6$ alkandiyl)carbonyl(C$_1$–C$_6$ alkanoxy)but-4-yl}naphthalene, or a pharmaceutically acceptable salt or solvate thereof;

4z) (syn, anti)-1-{1-(4-(10,11-difluorocyclopropyldibenzo-suber-5-yl)piperazin-1-yl)-2(R,S)-oxycarbonyloxy (C$_1$–C$_6$ alkandiyl)carbonyl(C$_1$–C$_6$ alkanoxy)pent-5-yl}naphthalene, or a pharmaceutically acceptable salt or solvate thereof;

4aa) (syn, anti)-1-{1-(4-(10,11-difluorocyclopropyldibenzo-suber-5-yl)piperazin-1-yl)-2(R,S)-oxycarbonyloxy (C$_1$–C$_6$ alkandiyl)carboxybut-4-yl}naphthalene, or a pharmaceutically acceptable salt or solvate thereof;

4bb) (syn, anti)-1-{1-(4-(10,11-difluorocyclopropyldibenzo-suber-5-yl)piperazin-1-yl)-2(R,S)-oxycarbonyloxy (C$_1$–C$_6$ alkandiyl)carboxypent-5-yl}naphthalene, or a pharmaceutically acceptable salt or solvate thereof;

4cc) (syn, anti)-1-{1-(4-(10,11-difluorocyclopropyldibenzo-suber-5-yl)piperazin-1-yl)-2(R,S)-oxycarbonyl(C$_1$–C$_6$ alkandiyl)carboxybut-4-yl}naphthalene, or a pharmaceutically acceptable salt or solvate thereof;

4dd) (syn, anti)-1-{1-(4-(10,11-difluorocyclopropyldibenzo-suber-5-yl)piperazin-1-yl)-2(R,S)-oxycarbonyl(C$_1$–C$_6$ alkandiyl)carbonyl(C$_1$–C$_6$ alkanoxy)pent-5-yl}naphthalene, or a pharmaceutically acceptable salt or solvate thereof; and mixtures thereof.

A preferred compound of the invention is a compound of Formula (CS) as follows:

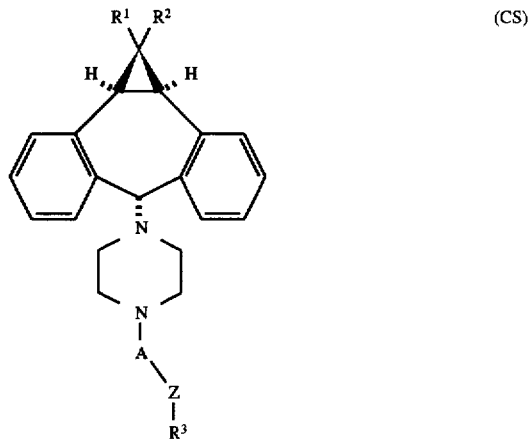

where: R$^1$, R$^2$, R$^3$, A and Z all have the said definition as above.

Another preferred compound of the invention is a compound of Formula (C1):

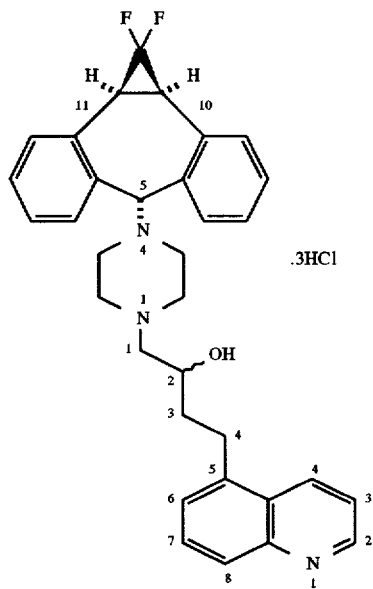

which is a mixture of the trihydrochloride salts of the 2(R) and 2(S) stereoisomers of anti-5-{1-(4-(10,11-difluorocyclopropyldibenzosuber-5-yl)piperazin-1-yl)-2-hydroxybut-4-yl}quinoline. The name for this mixture is anti-5-{1-(4-(10,11-difluorocyclopropyldibenzosuber-5-yl)piperazin-1-yl)-2(R,S)-hydroxybut-4-yl}quinoline·3HC$_1$. Another preferred compound is a compound of Formula (C$_2$):

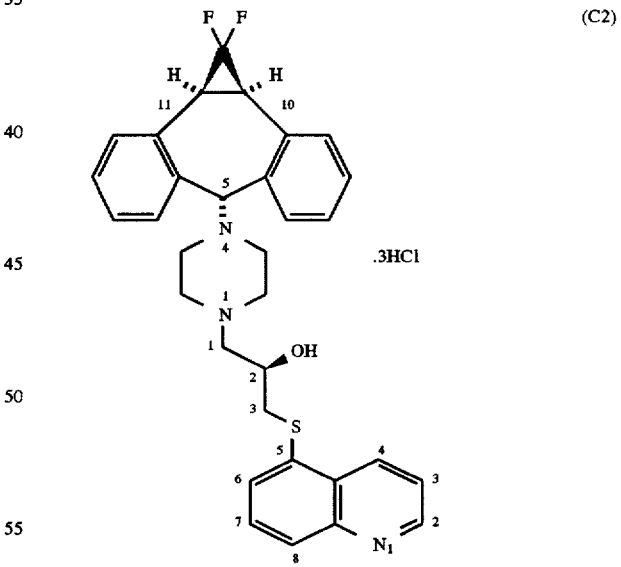

namely, anti-5-(1-(4-(10,11-difluorocyclopropyldibenzosuber-5-yl)piperazin-1-yl)-2(R)-hydroxyprop-3-ylthio}quinoline·3HC$_1$.

The compounds of Formula (C) can be prepared by reacting a 10,11-(optionally mono or dihalo) cyclopropyldibenzosuber-5-ylpiperazine of Formula (A)

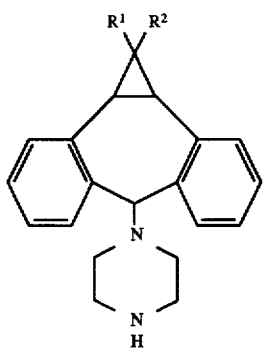

Formula (A)

where $R^1$ and $R^2$ can be hydrogen or halo as follows.

To make compounds of Formula (C) where Z is –CH2– and A is (–CH2–)d where d is 2, 3 or 4, a compound of Formula (A) is reacted with an aryl-($C_3$–$C_5$)alkandiyl-halide of Formula (B1):

$R^3$–(CH$_2$)$_c$–X   Formula (B1), where $R^3$ is as defined previously, c is 3, 4, or 5 and X is halo.

The 10,11-(optionally mono or dihalo)cyclopropyldibenzosuber-5-ylpiperazine compounds of Formula (A) can be made using the techniques described in PCT Patent Application PCT/US94/04215 (Publication No. WO 94/24107), pages 10–12. Briefly, the synthesis can be accomplished using a four step process as follows:

1) Dibenzosuberenone (commercially available from Aldrich Chemical Company, Milwaukee, Wisconsin) is converted to 10,11-(optionally mono or dihalo)cyclopropyldibenzosubernone by reacting the dibenzosuberenone with a suitable acetate reagent. The suitable acetate reagent is selected for its ability to add the desired substituents for $R^1$ and $R^2$ to the cyclopropyl ring, e.g. using sodium chlorodifluoro-acetate or methyl trichloroacetate will result in $R^1$ and $R^2$ both being chloro and using ethyl trifluoroacetate will result in both $R^1$ and $R^2$ being fluoro.

2) 10,11-(optionally mono or dihalo)cyclo- propyldibenzosubernone is reacted with a reducing agent to convert the 5-ketone functional group into a 5-alcohol functional group.

3) The 10,11-(optionally mono or dihalo)cyclopropyldibenzosuber-5-ol is halogenated at the 5-position and then reacted with 1-piperazinecarboxaldehyde to cause a nucleophilic displacement of the halide at the 5-position resulting in the formation of a mixture of (syn, anti)-1-((10,11-optionally mono or dihalo) cyclopropyldibenzosuber- 5-yl)-4-formyl-piperazine. The mixture can be separated into its syn and anti components by any technique known in -the art, e.g. chromatography.

4) The selected syn- or anti-1-((10,11- optionally mono or dihalo)cyclopropyldibenzosuber-5-yl)-4- formyl-piperazine is refluxed in a solvent for a sufficient length of time to cleave the formyl group, creating the corresponding 1-((10, 11-optionally mono or dihalo)cyclopropyldibenzosuber-5-yl)piperazine of Formula (A).

The aryl-($C_3$–$C_5$)alkandiyl halide(s) of Formula (B1) can be made by using standard techniques to add an alkyl halide chain to an aromatic group. The aromatic group is selected to give the desired $R^3$ aryl group and the alkyl portion of the alkyl halide is selected to give the desired number (from 3–5) of –CH2– groups for the Z and A components of the compound of Formula (C). The preferred halide for the alkyl halide is iodide. One such synthesis is described in detail in U.S. Pat. No. 5,112,817 which is incorporated by reference. Once the compound of Formula (B1) is obtained, it is reacted thermally in a solvent with a compound of Formula (A), as described in previously incorporated U.S. Pat. No. 5,112, 817.

To make compounds of Formula (C) where Z is —S— and A is (—CH$_2$—)$_d$ where d is as above, a compound of Formula (A) is reacted with a thioaryl-($C_2$–$C_4$)alkandiyl-halide of Formula (B2):

$R^3$—S—(CH$_2$)$_p$–X   Formula (B2), where $R^3$ and X are as defined previously and p is 2, 3 or 4;

The thioaryl-($C_2$–$C_4$)alkandiyl halide(s) of Formula (B2) can be made by using known procedures to add an alkyl-halide chain to the sulfur atom of a $R^3$–SH thioaryl group. This addition is done such that the terminal carbon of the alkyl halide is attached to the sulfur of the thioaryl group. Thioaryl groups can be obtained commercially or synthesized using standard techniques known in the art; one such synthesis method being the addition of elemental sulfur to a $R^3$–I compound. Once a compound of Formula (B1) is obtained, it is reacted thermally in a solvent with a compound of Formula (A).

To make compounds of Formula (C) where Z is —CH2— and A is —CH2—CHR$^4$—(CH2)$_n$— where n is 1 or 2 and $R^4$ is —OH, a compound of Formula (A) is reacted with an aryl-($C_2$–$C_3$)alkandiyl-epoxide of Formula (B3):

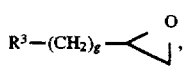   Formula (B3)

where $R^3$ is as defined previously and g is 2 or 3.

The aryl-($C_2$–$C_3$)alkandiyl-epoxide(s) of Formula (B3) can be made by converting arylaldehydes to aryl-($C_2$–$C_3$) alkandiyl-epoxide(s) using standard techniques known in the art. The number of carbons in the aldehyde chain is selected to yield the desired number of —CH2— groups in the —Z—A—component of Formula (C), and the aryl ring is selected to yield the desired $R^3$ component of Formula (C).

Arylaldehydes of the formula $R^3$–(CH2)g–CHO where g is 2 or 3, can be prepared by many methods known in the art. One such method is the two step conversion of a $R^3$- halo compound to a $R^3$-aldehyde. The first step in the conversion of a $R^3$-halo compound to an $R^3$-aldehyde is the coupling of an alkene- or alkyne- acetal with a $R^3$-halo compound using standard coupling reaction techniques, such as Heck coupling reaction techniques.

The acetal functional group is illustrated below:

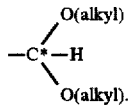

The carbon of the acetal functional group marked with an *, is the terminal carbon of the alkene or alkyne chain. For example: 1-propyne-3-dialkylacetal is

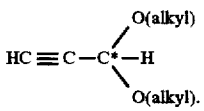

The alkyl groups in the acetal functionality are independently $C_1$–$C_6$ alkyl.

The preferred halo for the $R^3$-halo compound is iodo. The alkene or alkyne used in the alkene- or alkyne- acetal can be propene, propyne, butene or butyne. The selection of the alkene or alkyne depends on the number of carbon atoms desired in the —Z—A— component of the compounds of Formula (C).

Heck coupling reactions use a palladium catalyst and a suitable base, in a suitable non-reactive organic solvent such as acetonitrile, to couple alkene or alkyne chains with optional terminal functional groups or other terminal groups to haloaromatic compounds. The suitable base is any suitable base known in the art of Heck palladium catalyzed reactions, such as triethylamine. Similarly, the suitable solvent is any suitable non- reactive organic solvent, such as acetonitrile.

After the alkene- or alkyne-acetal moiety is coupled with the $R^3$ group, the double or triple bond is reduced to a single bond by hydrogenation using a suitable palladium on carbon catalyst. The acetal functional group is converted to an aldehyde functional group by subjecting it to acid hydrolysis.

Once the appropriate $R^3$-aldehyde is made, it can be converted to a $R^3$-$(C_2$-$C_3)$alkandiyl-epoxide of Formula (B3) by treating it with sodium hydride and sulfoxonium or sulfonium iodide. Once a compound of Formula (B3) is obtained, it is reacted with a compound of Formula (A), thermally in a solvent, as described previously.

To make compounds of Formula (C) where Z is —S— and A is -$CH_2$-$CHR^4$-$(CH_2)_n$- where n is 1 or 2 and $R^4$ is -OH, a compound of Formula (A) is reacted with a thioaryl-$(C_1$-$C_2)$ alkandiyl-epoxide of Formula (B4):

Formula (B4)

where $R^3$ is as defined previously and t is 1 or 2.

The thioaryl-$(C_1$-$C_2)$alkandiyl-epoxide(s) of Formula (B4) can be obtained by conversion of a haloaryl compound to a thioaryl compound and then coupling an alkandiyl-epoxide group to the thioaryl compound to form -the desired thioaryl- $(C_1$-$C_2)$alkandiyl-epoxide. The haloaryl compound is preferably of the formula $R^3$-I. The conversion of the haloaryl compound to a thioaryl can be done by reacting the haloaryl with a suitable organolithium reagent such as tert-butyllithium, and then adding sulfur to the reaction. After the thioaryl compound has been formed, it is reacted with a suitable reagent that is able to attach a $(C_1$-$C_2)$ alkandiyl epoxide chain to the sulfur linked to the aryl ring to form the thioaryl-$(C_1$-$C_2)$alkandiyl-epoxide(s) of Formula (B4). One such suitable reagent for this reaction is (2R)-(-)-glycidyl 3-nitrobenzenesulfonate. Once a compound of Formula (B4) is obtained, it is reacted with a compound of Formula (A), thermally in a solvent, as described previously.

When Z is —SO—, the compound of Formula (C) is made, and then the sulfur (—S—) that links $R^3$ with the —A— component of Formula (C) is oxidized to —SO— using one equivalent of oxidizing agent per equivalent of Formula (C) compound. The sulfur can be oxidized by the addition of a suitable oxidizing agent such as MCPBA (3-chloroperoxy- benzoic acid) or Oxonee (potassium peroxymonosulfate from E.I. DuPont de Nemours and Company) or sodium periodate. When Z is —$SO_2$— the same process is followed as when Z is SO, except that two equivalents of oxidizing agent per equivalent of Formula (C) is used. The oxidation of —S— to —SO— or —$SO_2$— can also take place before Formula (A) is coupled with Formula (B2) or Formula (B4).

To make a compound of Formula (C) where $R^4$ is

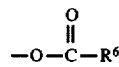

where $R^6$ is as described previously, a compound of Formula (C) is made, with $R^4$ a hydroxy group and then the hydroxy group is acylated using standard techniques known in the art.

To make a compound of Formula (C) where $R^4$ is

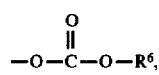

where $R^6$ is as described previously, a compound of Formula (C) is made, with $R^4$ a hydroxy group and then the hydroxy group is converted to

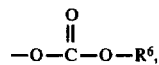

by using standard techniques known in the art.

Isolation and purification of the compounds and intermediates can be effected, if desired, by any suitable separation or purification procedure such as, for example, filtration, extraction, crystallization, column chromatography, thin-layer chromatography or thick-layer chromatography, or combinations of these procedures.

The compounds of Formula (C) can be converted to corresponding acid addition salts. The conversion is accomplished by treatment with a stoichiometric amount of an appropriate acid, which appropriate acid includes inorganic acids, such as hydrochloric acid, hydrobromic acid, sulfuric acid (giving the sulfate and bisulfate as acetic salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluene-sulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methylbicyclo[2.2.2]oct-2-ene-l- carboxylic acid, glucoheptonic acid, 4,4'-methylenebis(3- hydroxy-2-naphthoic) acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like. In the salt-forming step of this invention, the free base is typically dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent, or by evaporation of the solvent or by cooling the solution.

In the step of liberating the free base of Formula (C) according to the invention the acid addition salts of the compounds of Formula (C) can be decomposed to the corresponding free bases by treatment with an excess of a suitable base, such as ammonia or sodium bicarbonate, typically in the presence of an aqueous solvent, and at a temperature between between OC and 50° C. The free base is isolated by conventional means, such as extraction with an organic solvent. The stoichiometric excess must take into account the number of equivalents of acid bound by the base of Formula (C).

As stated above, the present invention includes solvates of the compounds of Formula (C) and the pharmaceutically acceptable salts therein. A particular compound of the present invention or a pharmaceutically acceptable salt thereof may form solvates with water or common organic solvents. Such solvates are included within the scope of claimed compounds of the present invention.

The compounds of the present invention are useful as drug and multidrug resistance modulators. They are useful for treating drug and multidrug resistance after resistance becomes clinically evident, and can also be administered at the time of initial drug therapy, before any clinical resistance becomes evident, to enhance the activity of drugs from the beginning of drug administration.

The compounds of the present invention are particularly useful for the treatment of drug resistant and multidrug resistant cancer and drug resistant malaria.

The compounds of the present invention are also useful for enhancing the oral bioavailability of a drug.

The compounds of the present invention are also useful for enhancing bioavailability of a drug to the brain.

As stated above, the present invention includes mixtures of the compounds or pharmaceutically acceptable salts or solvates of Formula (C). Preferred mixtures consist of racemic mixtures containing at least one pair of enantiomers. As stated previously, one such preferred mixture is a mixture of the trihydrochloride salts of the 2(R) and 2(S) enantiomers of anti-5-{1-(4-(10,11-difluorocyclopropyldibenzosuber-5-yl)piperazin-1-yl)-2-hydroxybut-4-yl}quinoline.

When in vitro testing for multidrug resistance modulation with cancer chemotherapeutic drugs is conducted compounds are evaluated for their ability to show multidrug resistance modulation when coadministered with an oncolytic. In vitro testing involves cell cytotoxicity assays, which are conducted by growing a P-glycoprotein- expressing multidrug resistant cell line such as CEM/VLBIOO (available from, among others, Dr. William Beck of St. Jude's Research Hospital in Tennessee), P388 VCR (available through DCT Repository, NCI, Frederick, MD) and CHCR5 (available from, among others, Dr. Victor Ling, Vancouver, B.C. Cancer Agency, Vancouver, B.C.) in the presence of an appropriate oncolytic and the multidrug resistance modulator as described below.

MTT, {3-(4,5-dimethyl-thiazol-2-yl)-2,5-diphenyl_tetrazolium bromide], DOX (doxorubicin), VP-16 (etoposide) A and VLB (vinblastine sulfate) can be obtained from Sigma Chemical Co. (St. Louis, MO). Taxol® (paclitaxel from Bristol-Myers Oncology) can be obtained from ICN Biomedicals, Inc. (Costa Mesa, CA). FBS (fetal bovine serum) can be purchased from Hyclone (Logan, UT). L-glutamine and Minimum Essential Media for suspension cultures (SMEM) can be purchased from GIBCO (Grand Island, NY). Tissue culture Seroclusters 96-well with round bottom wells can be obtained from Costar (Cambridge, MA). Tissue culture flask can be obtained from Corning Glass Works (Corning, NY).

The human leukemia cell lines parental CCRF–CEM and the multidrug resistant CEM/VLB$_{100}$ (selected with 100 ng/ml vinblastine) can be provided by William T. Beck (Beck, W. T., Mueller, M. J., and Tanzer L. R., Altered Surface Membrane Glycoproteins in Vinca Alkaloid - Resistant Human Leukemic Lymphoblast, Cancer Research, 39, 2070–2076 (1979)). The cells can be maintained in SMEM medium supplemented with 10% FBS and 2 mM L-glutamine in a humidified incubator with 95% air and 5% $C_{O2}$. Cell number can be determined using a Coulter Counter model ZM. Cells can be subcultured every 3–4 days.

Cell viability can be determined using a modified MTT dye reduction method (Denziot, F., Lang, R., "Rapid colorimetric assay for cell growth and survival modifications to the tetrazolium procedure giving improved sensitivity and reliability", J. Immunological Methods, 89, 271–277, (1986)). A brief description of this method is as follows: cells are harvested during the logarithmic growth phase, and seeded in 96-well serocluster plates at 7.5×103 cells/well and cultured for 72 hours in the presence of serially diluted oncolytics (VLB, DOX, VP-16 and Taxol®)±modulators. A single well assay is conducted using a fixed concentration of VLB (4 ng/ml) and modulator (5μM). The cytotoxicity of the modulator alone, at the same concentration is also determined. Modulators are prepared as 2 mM stocks in DMSO and added to the wells to give final concentrations ranging from 5 pM to 0.5 WM. After 72 hours, 20 gl of freshly prepared MTT (5 mg/ml in Dulbecco's phosphate buffered saline pH 7.5) is added to each well and placed for 4 hours in a 37° C. incubator. Cells are pelleted at 1800 R.P.M. for 10 minutes in a Sorvall RT6000B centrifuge. After centrifugation, 70 μl of medium is carefully removed from each well, and 100 gl of 2- propanol/0.04 N $HC_1$is added to dissolve the blue formazan stained cells. Cells are resuspended 5–10 times with a multipipettor or until no particulate matter was visible. Plates are immediately read on a Yitertek MCC/340 microplate reader (Flow Laboratories (McLean, VA) with a wavelength of 570 nm and a reference wavelength of 630 nm). Controls are measured in quadruplicate and modulators in duplicate.

$IC_{50}$'s are calculated from semilog dose response curves in the presence and absence of modulators for both the parent and resistant cell lines. The fold shift is calculated as the $IC_{50}$ for cells treated with oncolytic alone divided by the $IC_{50}$ for cells treated with oncolytic+modulator.

Taxol® was chosen as the test oncolytic for the studies reported herein due to the high level of resistance of the cell line CEM/VLB$_{100}$ to Taxol®. The $IC_{50}$ of Taxol® is determined in the presence of varying concentrations of the modifier, with the goal of achieving full reversal activity. Full reversal activity, or 100% reversal activity, is defined as the ability to achieve drug sensitivity in the multidrug resistant cell line which is equivalent to the sensitivity of the drug sensitive parental cell line. This data is presented here as $Rev_{50}$ and $Rev_{100}$. These numbers are defined as the lowest concentration of modifier (in μM) which can achieve 50% and 100% reversal activity, respectively.

When in vitro testing for drug resistance modulation of anti-malarial drugs is conducted, compounds are evaluated for their ability to exhibit drug resistance modulation when coadministered with an anti-malarial drug. The tests are conducted by placing the drug resistance modulator, the drug resistant malaria species, and the anti-malarial drug together and evaluating the drug resistant malaria species. The anti-malarial drug is a drug that the drug resistant malaria species is known to be resistant to. For example, the malaria species P. lophurae and P. cynumolgi are both resistant to the anti-malarial drug proguanil. Modulator activity is defined as the ability to achieve drug sensitivity to the anti-malarial drug in the drug resistant malaria species by coadministration of the anti-malarial drug and the drug resistance modulator of choice.

Further details on testing for reversal of drug resistance in various malaria species can be found in standard malaria references, such as: *Chemotherapy of Malaria*, by Covell, et al., ©1955 by World Health Organization, Geneva, and Practical Malariolocry, 2nd Edition, by Russell et al., ©1963 by Oxford University Press.

A simple screening test to determine oral bioavailability of a drug is to administer the drug orally and then test for the presence of the drug, or its metabolites, in the blood using standard blood analytical techniques. The test is run twice, once with the drug administered by itself and the second time the drug is administered in the presence of a drug resistance modulator. The results are compared to see how much more compound is orally bioavailable when the modulator is present. This test may be conducted on any mammal as it is not limited to humans.

An in vitro test for movement of a compound across the blood-brain barrier is begun by growing a confluent monolayer of either bovine brain endothelial or mouse brain capillary endothelial cells on a porous filter support to form a tight endothelium cell layer. The filter support is placed in a vessel containing phosphate buffered saline such that the only way for materials to get from one side of the vessel to another is through the cell layer/porous filter support.

A known compound (e.g. mannitol) is placed in the vessel on the serosal side of the cell layer/porous filter. Samples are removed from the non-serosal side of the cell layer/porous filter at 15–30 minute intervals over a 3–6 hour time period. Standard analytical techniques are used to determine the amount of known compound in the sample. This information is used to calculate the base line permeability of the cell layer/porous filter.

The drug of interest (e.g., oncolytic or anti- malarial) is then placed on one side of a vessel containing fresh saline and the same type of cell layer/porous filter barrier. Samples are removed from the other side at 15–30 minute intervals over a 3–6 hour time period. Standard analytical techniques are used to determine the amount of drug of interest in those samples. The amount of drug of interest that migrates across the barrier is indicative of the base line permeability of the cell layer/porous filter for that drug.

The test is then repeated, only this time the drug of interest and a drug resistance modulator are both placed on one side of a vessel prepared as before. Samples are pulled and tests are run as described above to see how much more of the drug of interest migrates across the cell layer/porous filter support with the drug resistance modulator being present.

An in vivo test to determine whether a drug administered to a mammal has crossed the blood brain barrier is to administer the drug to the mammal in any acceptable manner and then test for the presence of the drug, or its metabolites, in the mammal's cerebrospinal fluid. Like the test for oral bioavailability, this test to determine whether a drug has crossed the blood brain barrier may be conducted on any mammal as it is not limited to humans.

The compounds of the present invention may be administered to any mammal. Of all mammals, it is believed that humans will benefit the most from administration of these compounds.

The compounds of Formula (C) are administered at a therapeutically effective dosage, e.g., a dosage sufficient for the compound to:

(i) act as a drug or multidrug resistance modulator when coadministered with a treatment drug for a drug or multidrug resistant disease;

(ii) enhance the oral bioavailability of a drug; and/or (iii) enhance the bioavailability of a drug to the brain.

Treatment of a disease includes:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The compounds of Formula (C) are typically co- administered either before, during or after the administration of a drug that treats the disease in question. A preferred administration schedule is a continuous infusion over the 24 hour period during which the treatment drug is also administered. For cancer, a treatment drug would be a cancer chemotherapeutic agent, including, but not limited to, paclitaxel, doxorubicin, adriamycin, etoposide, teniposide, vinblastine, vincristine, mitomycin C, daunorubicin, and teniposide. For malaria a treatment drug would be an anti-malarial treatment drug, including but not limited to, pamaquine, primaquine, mepacrine, doxycycline, chloroquine, amodiaquine, quinine, quinidine, pyrimethamine, proguanil, mefloquine and sulphadiazine.

A daily dose of drug or multidrug resistance modulator for all methods of treatment described herein is from about 100 mg/$M^2$ of body surface area to about 1 g/$M^2$ of body surface area, preferably from about 200 mg/$M^2$ to about 800 mg/$M^2$ of body surface area and most preferably from about 400 mg/$M^2$ to about 500 mg/$M^2$ of body surface area. The frequency and amount of drug or multidrug resistance modulator compound administered will, of course, be dependent on the patient and the disease state being treated, the severity of the affliction, the manner and schedule of administration (e.g., oral administration one day prior to cancer chemotherapy as compared to intravenous administration during cancer chemotherapy) and the judgment of the prescribing physician.

The dosage level of the disease treatment drug is determined with reference to the state of the disease, the condition of the patient with the disease and the disease treatment drug being used. Standard medical references may be consulted to determine the dosage level for the disease treatment drugs described herein. The dosage level of the disease treatment drug is also adjusted for each recipient to maximize the efficacy of the disease treatment drug while minimizing any undesirable side effects. When a drug or multidrug resistance modulator is coadministered with a disease treatment drug, the dosage of the disease treatment drug may stay the same or be decreased, depending upon the efficacy of the drug or multidrug resistance modulator in performing its function.

In employing the compounds of this invention for treatment of drug or multidrug resistance, any pharmaceutically acceptable mode of administration can be used. The compounds of Formula (C) can be administered either alone or in combination with other pharmaceutically acceptable excipients. These include solid, semi-solid and liquid dosage forms, such as, for example, tablets, capsules, powders, liquids, suspensions, suppositories or the like. The compounds of Formula (C) can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions (also known as "formulations") will typically include a conventional pharmaceutical carrier, diluent or excipient and a compound of Formula (C). In addition, these compositions may include other medicinal agents, pharmaceutical agents, carriers, adjuvants, etc.

Depending upon the treatment drug and the disease being treated, the drug or multidrug resistance modulator may be administered in the same or different pharmaceutical composition as the treatment drug.

Generally, depending on the intended mode of administration, the pharmaceutically acceptable composition will contain from about 0.005% to about 95%, preferably from about 0.5% to about 50%, by weight of a compound of Formula (C), the remainder being suitable pharmaceutical excipients, carriers and diluents.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained - release formulations and the like.

Preferably the oral compositions will take the form of a pill or tablet. Thus, the composition will contain along with the active ingredient: a diluent such as lactose, sucrose, dicalcium phosphate, or the like; a lubricant such as magnesium stearate or the like; and a binder such as starch, gum acacia, gelatin, polyvinylpyrrolidone, cellulose and derivatives thereof; and the like.

Liquid pharmaceutically administrable compositions can, for example, be prepared by dissolving, dispersing, etc., an active compound as defined above and optional pharmaceutical adjuvants in a carrier, such as, for example, water, saline, mannitol, aqueous dextrose, glycerol, glycol, ethanol and the like, to thereby form a solution or suspension. If desired, the pharmaceutical composition to be administered may also contain minor amounts of non toxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 19th Edition, 1995.

Parenteral administration is generally characterized by injection (e.g. subcutaneously, intramuscularly, intravenously) or infusion through a central line. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, mannitol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc. A preferred liquid solution for parenteral administration contains an appropriate amount of compound in a 5% solution of mannitol in water.

A more recently devised approach for parenteral administration employs the implantation of a slow-release or sustained-release system, such that a constant level of adosage is maintained. See, e.g., U.S. Pat. No. 3,710,795.

The percentage of active compound contained in such parenteral compositions is highly dependent on the specific nature thereof; as well as the activity of the compound and the needs of the subject. However, percentages of active ingredient of from about 0.01% to about 10% in solution are employable, and will be higher if the composition is a solid which will be subsequently diluted to the above percentages. Preferably, the parenteral composition will contain from about 0.2% to about 2% of the active agent in solution.

The preferred manner of administering the active compound is, at the present time, infusion through a central line.

EXAMPLES

The following preparations and examples are given to enable those skilled in the art to more clearly understand and to practice the present invention. They should not be considered as limiting the scope of the invention, but merely as being illustrative and representative thereof.

The terms and abbreviations used in the instant examples have their normal meanings unless otherwise designated. For example: "OC" refers to degrees Celsius; "N" refers to normal or normality; "mol" refers to mole or moles; "mmol" refers to millimole or millimoles; "g" refers to gram or grams; "mg" refers to milligrams; "ml" refers to milliliter or milliliters; "mp" refers to melting point; "M" refers to molar or molarity; "psi" refers to pounds per square inch; "KPa" refers to kilopascals. "Mass spec." refers to mass spectrometry; "IR" refers to infrared spectroscopy; and "NMR" refers to nuclear magnetic resonance spectroscopy.

5-iodoquinoline           Example 1a

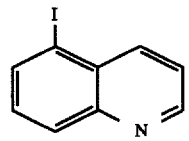

A suspension of 10 g (0.07 mol) of 5- aminoquinoline, 94 ml (0.7 mol) of isoamylnitrite and 100 ml of diiodomethane was heated at 80° C. for 2 hours. The reaction mixture was evaporated under reduced pressure at 60°–70° C. The residue was slurried with diethyl ether, decanted and the filtrate was evaporated under reduced pressure. The resulting residue was chromatographed on a silica gel column eluting with 3:1 hexane-ethyl acetate to yield 2.81 g of 5-iodoquinoline. $^1$H-NMR (CDC$_{l3}$, 300MHz) δ 7.42(d, 1H, J=7.7 Hz); 7.48 (dd, 1H, J=4.3 Hz); 8.1 (m, 2H,); 8.38 (d, 1H, J=8.5 Hz); 8.88 (m, 1H,). Mass spec. m/e=255=p.

5-quinoline-[1-propiolaldehyde diethyl acetal]  Example 1b

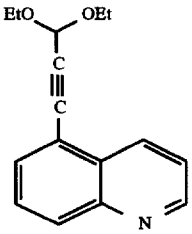

2.18 g (0.022 mol) of triethylamine were added to a suspension of 2.75 g (0.011 mol) of 5-iodoquinoline in acetonitrile (24 ml) and the solution formed on warming. The solution was allowed to cool briefly. To the solution were added 50 mg of triphenylphosphine, 50 mg of palladium(II) acetate and 3.1 ml (0.022 mol) of 3,3- zdiethoxy-1-propyne (propiolaldehyde diethylacetal). The reaction was heated at 80° C. for 1.5 hours. The reaction was poured into water and extracted with hexane. The hexane was removed under reduced pressure and the residue was chromatographed on a silica gel column and eluted with 1% methanol-dichloromethane to yield 1.44 g of 5-quinoline-[1- propiolaldehyde diethyl acetal]. $^1$H-NMR (CDC$_{l3}$, 300MHz) δ 1.3 (t, 6H, J=7.2 Hz); 3.73 (m, 2H,); 3.88 (m, 2H); 5.62 (s, 1H,); 7.48 (dd, 1H, J=8.5 and 4.2 Hz); 7.66 (d, 1H, J=7.4 Hz); 7.76 (d, 1H, J=7.2Hz); 8.1 (d, 1H, J=8.5Hz); 8.6 (d, 1H, J=8.5Hz); 8.94 (m, 1H). Mass spec. m/e=255=p.

5-quinoline-[1-propionaldehyde]  Example 1c

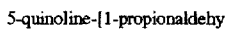
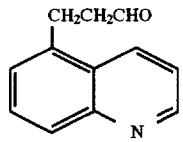

A mixture of 0.15 g of 5-quinoline-[1-propiol- aldehyde diethyl acetal] and 0.035 g of 10% palladium on carbon in ethanol (10 ml) was hydrogenated at 45 psi (310 KPa) for 1.5 hours. The catalyst was removed by filtration and the solvent was removed under reduced pressure. The residue was taken into 1.0 N HC$_l$(1 ml) and tetrahydrofuran (10 ml) and stirred 2 hours at ambient temperature which converted the acetal to the aldehyde functionality. The solvent was removed under reduced pressure and the residue was taken into ethyl acetate and washed with sodium bicarbonate solution. The solvent was removed under reduced pressure to obtain 63 mg of 5-quinoline-[1- propionaldehyde]. $^1$H-NMR (CDC$_{13, 300}$MHz) δ 2.95 (t, 2H, J=7.4 Hz); 3.43 (t, 2H, J=7.4Hz); 7.44 (m, 2H); 7.66 (t, 1H, J=7.4 Hz); 8.0 (d, 1H, J=8.5Hz); 8.33 (d, 1H, J=8.5Hz); 8.94 (m, 1H); 9.9 (s, 1H). Mass spec. m/e=186=

5-(3,4-epoxybut-1-yl)quinoline  Example 1d

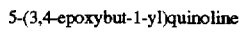
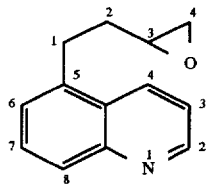

To a suspension of 0.47 g (2.1 mmol) of trimethylsulfoxonium iodide in dimethylsulfoxide (5 ml) was added 85 mg (2.1 mmol) of 60% sodium hydride. After 30 minutes, a solution of 0.33 g (1.93 mmol) of 5-quinoline- [1-propionaldehyde] in dimethylsulfoxide (7 ml) was added. After 30 minutes, the reaction was poured into cold brine and extracted with ethyl acetate. The organic layer was dried and the solvent was removed under reduced pressure and the residue was chromatographed on a silica gel column and eluted with 50% ethyl acetate-hexane to obtain 40 mg of 5-(3,4-epoxybut-1-yl)quinoline. $^1$H-NMR (CDC$_{13, 300}$MHz) δ 1.87 (m, 2H); 2.5 (m, 1H,); 3.03 (m, 1H); 3.24 (m, 2H,); 7.44 (m, 2H); 7.65 (t, 1H, J=7.4Hz ); 8.0 (d, 1H, J=8.5Hz); 8.4 (d, 1H, J=8.5Hz); 8.94 (d, 1H, J=4.2 Hz) Mass spec. m/e=199=p.

Example 1e
anti-5-{1-[4-(10,11-difluorocyclopropyldibenzosuber-5-yl) piperazin-1-yl]-2(R,S)-hydroxybut-4-yl}quinoline.3HCl

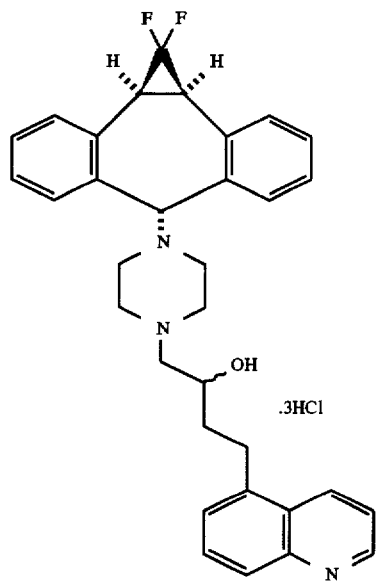

A solution of 31 mg (0.16 mmol) of 5-(3,4- epoxybut-1-yl)quinoline and 51 mg (0.16 mmol) of 4-N-(1'- (10,11-difluorocyclopropyldibenzosuber-5-yl)piperazine (obtained using the procedure(s) described in PCT Patent Application PCT/US94/04215, Publication Number WO 94/24107) in isopropyl alcohol (1.5 ml) was refluxed for 4.5 hours. The solvent was removed at reduced pressure and the residue was chromatographed on a silica gel column eluted with ethyl acetate followed by 5% methanol-dichloromethane. The residue was dissolved in ethyl alcohol (3ml), cooled and treated with anyhydrous hydrogen chloride gas. The reaction was evaporated under reduced pressure to yield 43 mg of a mixture of anti-5-(1-(4-(10,11-difluorocyclopropyl-dibenzosuber-5-yl)piperazin-1-yl)-2(R,S)-hydroxybut-4-yl}quinoline·3HC$_{l;}$ mp 160°–170° C. dec; $^1$H-NMR (CDC$_{l₃}$, 300MHz) (free base) δ 1.78 (m, 2H); 2.5 (m, 10 H); 3.19 (d, 2H, J=12.4 Hz); 3.19 (m, 1H) 3.37 (m, 1H); 3.75 (m, 1H); 3.93 (s, 1H); 7.2 (m, 8H); 7.44 (dd, 1H, J=8.5 and 4.2 Hz); 7.63 (t, 1H, J=7.4 Hz); 7.97 (d, 1H, J=8.5Hz); 8.45 (d, 1H, J=8.5Hz ); 8.9 (m, 1H). Mass spec. m/e=525=p.

(S)-5-(glycidyl)-thioquinoline  Example 2a

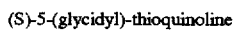
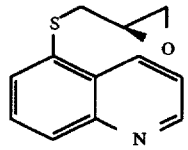

To a solution of 0.13 g (0.51 mmol) of 5-iodoquinoline in 4 ml of tetrahydrofuran at −78° C. was added 0.59 ml (1.0 mmol) of tert-butyllithium (1.7M in hexane). After 10 minutes, 20 mg (0.61 mmol) of sulfur were added and the cooling was removed. After 40 minutes, the reaction was cooled to 50C and 0.132 g (0.51 mmol) of (2R)-(—)-glycidyl 3-nitrobenzenesulfonate was added. After 30 minutes, the reaction was poured into cold brine, extracted with ethyl acetate, and concentrated under reduced pressure to an orange residue. The residue was chromatographed on a silica gel column and eluted with 2% methanol-dichloromethane to obtain 27 mg of (S)—5— (glycidyl)- thioquinoline. $^1$H-NMR (CDC$_{l3, 300}$ MHz) δ 2.41 (m, 1H); 2.72 (m, 1H,); 3.02 (t, 1H, J=4.4Hz); 3.16 (m, 2H); 7.45 (dd, 1H, J=8.5 and 4.2 Hz); 7.65 (m, 2H); 8.05 (d, 1H, J=8.0 Hz); 8.8 (d, 1H, J=8.7Hz); 8.93 (m, 1H ). Mass spec. m/e=217=p.

Example 2b
anti-5-{1-[4-(10,11-difluorocyclopropyldibenzosuber-5-yl)-piperazin-1-yl]-2(R)-hydroxyprop-3-ylthio}quinoline.3HCl

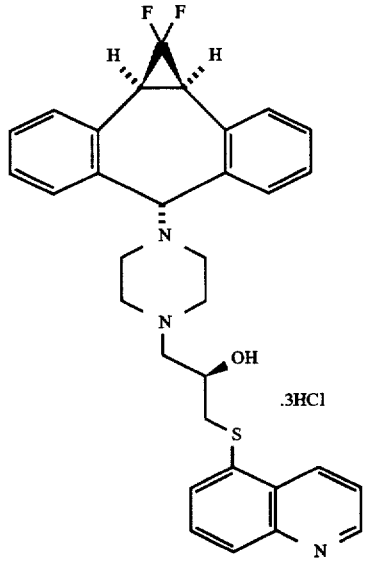

A mixture of 25 mg (0.12 mmol) of (S)-5- (glycidyl)-thioquinoline and 38 mg (0.12 mmol) of 4-N-(1'- (10,11-difluorocyclopropyldibenzosuber-5-yl)piperazine (obtained using the procedure(s) described in PCT Patent Application PCT/US94/04215, Publication Number WO 94/2407) in 2 ml of isopropyl alcohol was refluxed for 3 hours, after which the solvent was removed under reduced pressure and the residue was chromatographed on a silica gel column and eluted with 2–3% methanol in dichloromethane to obtain 39 mg of anti-5-{1-(4-(10,11-difluorocyclopropyldi-benzosuber-5-yl)piperazin-1-yl)-2(R)-hydroxyprop-3-ylthio}quinoline·3HC$_1$; mp 125°–130° C. dec; $^1$H-NMR (CDC$_{l3, 300}$MHz) δ 2.45 (m, 1OH ); 3.05 (m, 2H); 3.16 (d, 2H, J=12.4Hz); 3.86 (m, 1H); 3.9 (s, 1H); 7.2 (m, 8H); 7.45 (dd, 1H, J=8.5 and 4.2 Hz); 7.65 (m, 2H); 8.0 (d, 1H, J=8.0 Hz); 8.75 (d, 1H, J=8.7Hz); 8.93 (m, 1H). Mass spec. m/e =543=p. Anal. Calcd.: C, 70.70; H, 5.75; N, 7.73; S, 5.90. Anal. Actual: C, 69.98; H, 5.78; N, 7.34; S, 5.65.

EXAMPLE 3

The compound of Example 1e (anti-5-{1-(4-(10,11-difluorocyclopropyldibenzosuber-5-yl)piperazin-1-yl)- 2(R, S)-hydroxybut-4-yl}quinoline·3HC$_1$) and Example 2b (anti-5-{1-(4-(10,11-difluorocyclopropyldibenzosuber-5-yl)piperazin-1-yl)-2(R)-hydroxyprop-3-ylthio}quinoline 3HC$_1$) both showed potent MDR Reversal Activity in the previously-described p-glycoprotein MDR assay with Taxol®.

| Example | Rev$_{100}$ (μM) | Rev$_{50}$ (μM) |
|---|---|---|
| 1e | >1.0 | 1.0 |
| 2b | 0.50 | 0.25 |
| Comparative* | 0.10 | 0.050 |

*The Comparative Example is anti-5-{1-(4-(10,11-difluorocyclopropyldibenzosuber-5-yl)piperazin-1-yl)-2(R)-hydroxyprop-3-oxy}quinoline.

The following formulation examples are illustrative only and are not intended to limit the scope of the invention in any way. "Active ingredient" means a compound of Formula (C) or a pharmaceutically acceptable 5 salt or solvate thereof.

Formulation 1

Hard gelatin capsules are prepared using the 10 following ingredients:

| | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

| | Quantity (mg/capsule) |
|---|---|
| Active ingredient | 250 |
| Cellulose, micro crystalline | 400 |
| Silicon dioxide, fumed | 10 |
| Stearic acid | 5 |
| Total | 665 mg |

The components are blended and compressed to form tablets each weighing 665 mg.

Formulation 3

Tablets, each containing 60 mg of active ingredient, are made as follows:

| | Quantity (mg/tablet) |
|---|---|
| Active ingredient | 60 |
| Starch | 45 |
| Micro crystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing 10 polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 4

Capsules, each containing 80 mg of active ingredient, are made as follows:

|  | Quantity (mg/capsule) |
|---|---|
| Active ingredient | 80 |
| Starch | 59 |
| Micro crystalline cellulose | 59 |
| Magnesium stearate | 2 |
| Total | 200 |

The active ingredient, cellulose, starch, and magnesium stearate are blended, passed through a No. 45 mesh U.S. sieve, and filled into hard gelatin capsules in 200 mg quantities.

Formulation 5

Suppositories, each containing 225 mg of active ingredient, are made as follows:

|  | Quantity (mg/unit) |
|---|---|
| Active ingredient | 225 |
| Saturated fatty acid glycerides | 2,000 |
| Total | 2,225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 50 mg of active ingredient per 5 mL dose, are made as follows:

|  | Quantity |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

Purified water to total 5 mL The active ingredient is passed through a No. 45 mesh U.S. sieve and mixed with the sodium carboxymethyl cellulose and syrup to form a smooth paste. The benzoic 10 acid solution, flavor and color are diluted with a portion of the water and added, with stirring. Sufficient water is then added to produce the required volume.

Formulation 7

An intravenous formulation may be prepared as follows:

|  | Quantity |
|---|---|
| Active ingredient | 100 mg |
| Isotonic saline | 1,000 mL |

What is claimed is:
1. A compound of Formula (C):

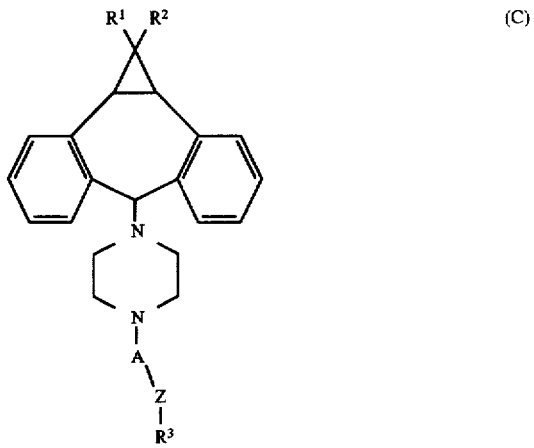

where:
$R^1$ and $R^2$ are independently hydrogen or halo;
A is —CH2—CH2— or —CH2—CHR$^4$—(CH$_2$)$_n$—; where n is 1 or 2;
$R^4$ is —H, —OH, or —R$^5$;

—R$^5$ is —O—C(=O)—R$^6$ or —O—C(=O)—O—R$^6$, or —R$^5$;
—R$^5$ is
—R$^6$ is C$_1$–C$_4$ or

—(CH$_2$)$_m$—C(=O)—OR$^7$;

where: m is 1, 2, 3, 4, 5 or 6, and R$^7$ is —H or C$_1$–C$_6$ alkyl; providing when A is —CH$_2$—CHR$^4$—(CH$_2$)$_n$—, A and Z are oriented as —CH$_2$—CHR$^4$—(CH$_2$)$_n$—Z—;
Z is selected from the group consisting of —S—, —S(O)$_w$—, and —CH$_2$—, where w is 1 or 2;
$R^3$ is an aryl moiety selected from the group consisting of phenyl, substituted phenyl, heteroaryl, substituted heteroaryl, polynuclear aryl and substituted polynuclear aryl; with the proviso that Z is connected to $R^3$ at a ring carbon atom of $R^3$; and pharmaceutically acceptable salts or solvates thereof.
2. A compound of claim 1 in which
$R^1$ and $R^2$ are both halo;
$R^3$ is selected from the group consisting of quinolyl, substituted quinolyl, isoquinolyl, substituted quinolyl, indolinyl, substituted indolinyl, naphthyl and substituted naphthyl;
A is -CH$_2$-CHR$^4$—(CH$_2$)$_n$—, $R^4$ is —OH, n is 1 or 2; and Z is —S— or —CH$_2$—.

3. A compound of claim 1 selected from the group consisting of 1a) (syn, anti)-5-{1-(4-(10,11-difluorocyclopropyldibenzo- suber-5-yl)piperazin-1-yl)prop-3-yl}quinoline, or a pharmaceutically acceptable salt or solvate thereof;

1b) (syn, anti)-5-{1-(4-(10,11-difluorocyclopropyldibenzo-suber-5-yl)piperazin-1-yl)but-4-yl}quinoline, or a pharmaceutically acceptable salt or solvate thereof;

1c) (syn, anti)-5-{1-(4-(10,11-difluorocyclopropyldibenzo-suber-5-yl)piperazin-1-yl)pent-5-yl)quinoline, or a pharmaceutically acceptable salt or solvate thereof;

1d) (syn, anti)-5-{1-(4-(10,11-difluorocyclopropyldibenzo- suber-5-yl)piperazin-1-yl) eth-2-ylthio}quinoline, or a pharmaceutically acceptable salt or solvate thereof;

1e) (syn, anti)-5-{1-(4-(10,11-difluorocyclopropyldibenzo- suber-5-yl)piperazin-1-yl)prop-3-ylthio[]quinoline, or a pharmaceutically acceptable salt or solvate thereof;

1f) (syn, anti)-5-{1-(4-(10,11-difluorocyclopropyldibenzo-suber-5-yl)piperazin-1-yl)but-4-ylthiolquinoline, or a pharmaceutically acceptable salt or solvate thereof;

1g) (syn, anti)-5-{1-(4-(10,11-difluorocyclopropyldibenzo- suber-5-yl)piperazin-1-yl)eth-2-ylsulfinyl}quinoline, or a pharmaceutically acceptable salt or solvate thereof;

1h) (syn, anti)-5-{1-(4-(10,11-difluorocyclopropyldibenzo- suber-5-yl)piperazin-1-yl)prop-3-ylsulfinyl}quinoline, or a pharmaceutically acceptable salt or solvate thereof;

1i) (syn, anti)-5-{1-(4-(10,11-difluorocyclopropyldibenzo- suber-5-yl)piperazin-1-yl)but-4-ylsulfinyl}quinoline, or a pharmaceutically acceptable salt or solvate thereof;

1j) (syn, anti)-5-{1-(4-(10,11-difluorocyclopropyldibenzo- suber-5-yl)piperazin-1-yl)eth-2-ylsulfonyl}quinoline, or a pharmaceutically acceptable salt or solvate thereof;

1k) (syn, anti)-5-{1-(4-(10,11-difluorocyclopropyldibenzo- suber-5-yl)piperazin-1-yl)prop-3-ylsulfonyl}quinoline, or a pharmaceutically acceptable salt or solvate thereof;

1l) (syn, anti)-5-{1-(4-(10,11-difluorocyclopropyldibenzo- suber-5-yl)piperazin-1-yl)but-4-ylsulfonyl}quinoline, or a pharmaceutically acceptable salt or solvate thereof;

1m) (syn, anti)-5-{1-(4-(10,11-difluorocyclopropyldibenzo- suber-5-yl)piperazin-1-yl)-2(R,S)-hydroxybut-4- yl}quinoline, or a pharmaceutically acceptable salt or solvate thereof;

1n) (syn, anti)-5-{1-(4-(10,11-difluorocyclopropyldibenzo- suber-5-yl)piperazin-1-yl)-2(R,S)-hydroxypent-5- yl}quinoline, or a pharmaceutically acceptable salt or solvate thereof;

1o) (syn, anti)-5-{1-(4-(10,11-difluorocyclopropyldibenzo- suber-5-yl)piperazin-1-yl)-2(R,S)-hydroxyprop-3-ylthio}- quinoline, or a pharmaceutically acceptable salt or solvate thereof;

1p) (syn, anti)-5-{1-(4-(10,11-difluorocyclopropyldibenzo- suber-5-yl)piperazin-1-yl)-2(R,S)-hydroxybut-4- ylthio}quinoline, or a pharmaceutically acceptable salt or solvate thereof;

1q) (syn, anti)-5-{1-(4-(10,11-difluorocyclopropyldibenzo- suber-5-yl)piperazin-1-yl)-2(R,S)-hydroxyprop-3- ylsulfinyl}quinoline, or a pharmaceutically acceptable salt or solvate thereof;

1r) (syn, anti)-5-{i-(4-(10,11-difluorocyclopropyldibenzo- suber-5-yl)piperazin-1-yl)-2(R,S)-hydroxybut-4- ylsulfinyl}quinoline, or a pharmaceutically acceptable salt or solvate thereof;

1s) (syn, anti)-5-{i-(4-(10,11-difluorocyclopropyldibenzo- suber-5-yl)piperazin-1-yl)-2(R,S)-hydroxyprop-3- ylsulfonyl}-quinoline, or a pharmaceutically acceptable salt or solvate thereof;

1t) (syn, anti)-5-{1-(4-(10,11-difluorocyclopropyldibenzo- suber-5-yl)piperazin-1-yl)-2(R,S)-hydroxybut-4-ylsulfonyl}- quinoline, or a pharmaceutically acceptable salt or solvate thereof;

1u) (syn, anti)-5-{1-(4-(10,11-difluorocyclopropyldibenzo- suber-5-yl)piperazin-1-yl)-2(R,S)-oxy($C_1$–$C_6$ alkanoyl)but-4- yl}quinoline, or a pharmaceutically acceptable salt or solvate thereof;

1v) (syn, anti)-5-{1-(4-(10,11-difluorocyclopropyldibenzo- suber-5-yl)piperazin-1-yl)-2(R,S)-oxy($C_1$–$C_6$ alkanoyl)pent- 5-yl]quinoline, or a pharmaceutically acceptable salt or solvate thereof;

1w) (syn, anti)-5-{1-(4-(10,11-difluorocyclopropyldibenzo- suber-5-yl)piperazin-1-yl)-2(R,S)-oxycarbonyl($C_1$–$C_6$ alkanoxy)but-4-yl}quinoline, or a pharmaceutically acceptable salt or solvate thereof;

1x) (syn, anti)-5-{1-(4-(10,11-difluorocyclopropyldibenzo- suber-5-yl)piperazin-1-yl)-2(R,S)-oxycarbonyl($C_1$–$C_6$ alkanoxy)pent-5-yl}quinoline, or a pharmaceutically acceptable salt or solvate thereof;

1y) (syn, anti)-5-{1-(4-(10,11-difluorocyclopropyldibenzo- suber-5-yl)piperazin-1-yl)-2(R,S)-oxycarbonyloxy($C_1$–$C_6$ alkandiyl)carbonyl ($C_1$–$C_6$ alkanoxy)but-4-yl}quinoline, or a pharmaceutically acceptable salt or solvate thereof;

1z) (syn, anti)-5-{1-(4-(10,11-difluorocyclopropyldibenzo- suber-5-yl)piperazin-1-yl)-2(R,S)-oxycarbonyloxy(Cl–$C_6$ alkandiyl)carbonyl ($C_1$–$C_6$ alkanoxy)pent-5-yl}quinoline, or a pharmaceutically acceptable salt or solvate thereof;

1aa) (syn, anti)-5-{1-(4-(10,11-difluorocyclopropyldibenzo- suber-5-yl)piperazin-1-yl)-2(R,S)-oxycarbonyloxy($C_1$–$C_6$ alkandiyl) carboxybut-4-yl}quinoline, or a pharmaceutically acceptable salt or solvate thereof;

1bb) (syn, anti)-5-{1-(4-(10,11-difluorocyclopropyldibenzo- suber-5-yl)piperazin-1-yl)-2(R,S)-oxycarbonyloxy($C_1$–$C_6$ alkandiyl) carboxypent-5-yl}quinoline, or a pharmaceutically acceptable salt or solvate thereof;

1cc) (syn, anti)-5-{1-(4-(10,11-difluorocyclopropyldibenzo- suber-5-yl)piperazin-1-yl)-2(R,S)-oxycarbonyl($C_1$–$C_6$ alkandiyl)-carboxybut-4-yl}quinoline, or a pharmaceutically acceptable salt or solvate thereof;

1dd) (syn, anti)-5-{1-(4-(10,11-difluorocyclopropyldibenzo- suber-5-yl)piperazin-1-yl)-2(R,S)-oxycarbonyl($C_1$–$C_6$ alkandiyl)-carbonyl ($C_1$–$C_6$ alkanoxy)pent-5-yl}quinoline, or a pharmaceutically acceptable salt or solvate thereof;

2a) (syn, anti)-5-{1-(4-(10,11-difluorocyclopropyldibenzo- suber-5-yl)piperazin-1-yl)prop-3-yl}isoquinoline, or a pharmaceutically acceptable salt or solvate thereof;

2b) (syn, anti)-5-{1-(4-(10,11-difluorocyclopropyldibenzo- suber-5-yl)piperazin-1-yl)but-4-yl}isoquinoline, or a pharmaceutically acceptable salt or solvate thereof;

2c) (syn, anti)-5-fl-(4-(10,11-difluorocyclopropyldibenzo- suber-5-yl)piperazin-1-yl)pent-5-yl}isoquinoline, or a pharmaceutically acceptable salt or solvate thereof;

2d) (syn, anti)-5-{1-(4-(10,11-difluorocyclopropyldibenzo- suber-5-yl)piperazin-1-yl)eth-2-ylthio}isoquinoline, or a pharmaceutically acceptable salt or solvate thereof;

2e) (syn, anti)-5-{1-(4-(10,11-difluorocyclopropyldibenzo- suber-5-yl)piperazin-1-yl)prop-3-ylthio}isoquinoline, or a pharmaceutically acceptable salt or solvate thereof;

2f) (syn, anti)-5-{1-(4-(10,11-difluorocyclopropyldibenzo- suber-5-yl)piperazin-1-yl)but-4-ylthioyisoquinoline, or a pharmaceutically acceptable salt or solvate thereof;

2g) (syn, anti)-5-{1-(4-(10,11-difluorocyclopropyldibenzo- suber-5-yl)piperazin-1-yl)eth-2-ylsulfinyl}isoquinoline, or a pharmaceutically acceptable salt or solvate thereof;

2h) (syn, anti)-5-{1-(4-(10,11-difluorocyclopropyldibenzo- suber-5-yl)piperazin-1-yl)prop-3-ylsulfinyllisoquinoline, or a pharmaceutically acceptable salt or solvate thereof;

2i) (syn, anti)-5-{1-(4-(10,11-difluorocyclopropyldibenzo- suber-5-yl)piperazin-1-yl)but-4-ylsulfinyl}isoquinoline, or a pharmaceutically acceptable salt or solvate thereof;

2j) (syn, anti)-5-fl-(4-(10,11-difluorocyclopropyldibenzo-suber-5-yl)piperazin-1-yl)eth-2-ylsulfonyl}isoquinoline, or a pharmaceutically acceptable salt or solvate thereof;

2k) (syn, anti)-5-{1-(4-(10,11-difluorocyclopropyldibenzo- suber-5-yl)piperazin-1-yl)prop-3-ylsulfonyl}isoquinoline, or a pharmaceutically acceptable salt or solvate thereof;

2l) (syn, anti)-5-{1-(4-(10,11-difluorocyclopropyldibenzo- suber-5-yl)piperazin-1-yl)but-4-ylsulfonyl}isoquinoline, or a pharmaceutically acceptable salt or solvate thereof;

2m) (syn, anti)-5-{1-(4-(10,11-difluorocyclopropyldibenzo- suber-5-yl)piperazin-1-yl)-2(R,S)-hydroxybut-4- yl}isoquinoline, or a pharmaceutically acceptable salt or solvate thereof;

2n) (syn, anti)-5-{1-(4-(10,11-difluorocyclopropyldibenzo- suber-5-yl)piperazin-1-yl)-2(R,S)-hydroxypent-5- yl}isoquinoline, or a pharmaceutically acceptable salt or solvate thereof;

2o) (syn, anti)-5-{1-(4-(10,11-difluorocyclopropyldibenzo- suber-5-yl)piperazin-1-yl)-2(R,S)-hydroxyprop-3- ylthio}isoquinoline, or a pharmaceutically acceptable salt or solvate thereof;

2p) (syn, anti)-5-{1-(4-(10,11-difluorocyclopropyldibenzo- suber-5-yl)piperazin-1-yl)-2(R,S)-hydroxybut-4- ylthio}isoquinoline, or a pharmaceutically acceptable salt or solvate thereof;

2q) (syn, anti)-5-{1-(4-(10,11-difluorocyclopropyldibenzo- suber-5-yl)piperazin-1-yl)-2(R,S)-hydroxyprop-3- ylsulfinyl}-isoquinoline, or a pharmaceutically acceptable salt or solvate thereof;

2r) (syn, anti)-5-{1-(4-(10,11-difluorocyclopropyldibenzo- suber-5-yl)piperazin-1-yl)-2(R,S)-hydroxybut-4- ylsulfinyl}isoquinoline, or a pharmaceutically acceptable salt or solvate thereof;

2s) (syn, anti)-5-{1-(4-(10,11-difluorocyclopropyldibenzo- suber-5-yl)piperazin-1-yl)-2(R,S)-hydroxyprop-3- ylsulfonylyisoquinoline, or a pharmaceutically acceptable salt or solvate thereof;

2t) (syn, anti)-5-{1-(4-(10,11-difluorocyclopropyldibenzo- suber-5-yl)piperazin-1-yl)-2(R,S)-hydroxybut-4- ylsulfonyl}isoquinoline, or a pharmaceutically acceptable salt or solvate thereof;

2u) (syn, anti)-5-{1-(4-(10,11-difluorocyclopropyldibenzo- suber-5-yl)piperazin-1-yl)-2(R,S)-oxy($C_1$-$C_6$ alkanoyl)but-4- yl}isoquinoline, or a pharmaceutically acceptable salt or solvate thereof;

2v) (syn, anti)-5-{1-(4-(10,11-difluorocyclopropyldibenzo- suber-5-yl)piperazin-1-yl)-2(R,S)-oxy($C_1$-$C_6$ alkanoyl)pent-5-yl}isoquinoline, or a pharmaceutically acceptable salt or solvate thereof;

2w) (syn, anti)-5-{1-(4-(10,11-difluorocyclopropyldibenzo- suber-5-yl)piperazin-1-yl)-2(R,S)-oxycarbonyl($C_1$-$C_6$ alkanoxy)but-4-yl}isoquinoline, or a pharmaceutically acceptable salt or solvate thereof;

2x) (syn, anti)-5-{1-(4-(10,11-difluorocyclopropyldibenzo- suber-5-yl)piperazin-1-yl)-2(R,S)-oxycarbonyl($C_1$-$C_6$ alkanoxy)pent-5-yllisoquinoline, or a pharmaceutically acceptable salt or solvate thereof;

2y) (syn, anti)-5-{1-(4-(10,11-difluorocyclopropyldibenzo- suber-5-yl)piperazin-1-yl)-2(R,S)-oxycarbonyloxy($C_1$-$C_6$ alkandiyl)carbonyl ($C_1$-$C_6$ alkanoxy)but-4-yl}isoquinoline, or a pharmaceutically acceptable salt or solvate thereof;

2z) (syn, anti)-5-{1-(4-(10,11-difluorocyclopropyldibenzo- suber-5-yl)piperazin-1-yl)-2(R,S)-oxycarbonyloxy($C_1$-$C_6$ alkandiyl)carbonyl (CI-$C_6$ alkanoxy)pent-5-yl}isoquinoline, or a pharmaceutically acceptable salt or solvate thereof;

2aa) (syn, anti)-5-{1-(4-(10,11-difluorocyclopropyldibenzo- suber-5-yl)piperazin-1-yl)-2(R,S)-oxycarbonyloxy($C_1$-$C_6$ alkandiyl) carboxybut-4-yl}isoquinoline, or a pharmaceutically acceptable salt or solvate thereof;

2bb) (syn, anti)-5-{1-(4-(10,11-difluorocyclopropyldibenzo- suber-5-yl)piperazin-1-yl)-2(R.S)-oxycarbonyloxy($C_1$-$C_6$ alkandiyl) carboxypent-5-yl}isoquinoline, or a pharmaceutically acceptable salt or solvate thereof;

2cc) (syn, anti)-5-{1-(4-(10,11-difluorocyclopropyldibenzo- suber-5-yl)piperazin-1-yl)-2(R,S)-oxycarbonyl($C_1$-$C_6$ alkandiyl)carboxybut-4-yl}isoquinoline, or a pharmaceutically acceptable salt or solvate thereof;

2dd) (syn, anti)-5-{1-(4-(10,11-difluorocyclopropyldibenzo- suber-5-yl)piperazin-1-yl)-2(R,S)-oxycarbonyl($C_1$-$C_6$ alkandiyl)carbonyl ($C_1$-$C_6$ alkanoxy)pent-5-yl}isoquinoline, or a pharmaceutically acceptable salt or solvate thereof;

3a) (syn, anti)-4-{1-(4-(10,11-difluorocyclopropyldibenzo- suber-5-yl)piperazin-1-yl)prop-3-yl}indole, or a pharmaceutically acceptable salt or solvate thereof;

3b) (syn, anti)-4-{1-(4-(10,11-difluorocyclopropyldibenzo- suber-5-yl)piperazin-1-yl)but-4-yl}indole, or a pharmaceutically acceptable salt or solvate thereof;

3c) (syn, anti)-4-{1-(4-(10,11-difluorocyclopropyldibenzo- suber-5-yl)piperazin-1-yl)pent-5-yl}indole, or a pharmaceutically acceptable salt or solvate thereof;

3d) (syn, anti)-4-{1-(4-(10,11-difluorocyclopropyldibenzo- suber-5-yl)piperazin-1-yl) eth-2-ylthio}indole, or a pharmaceutically acceptable salt or solvate thereof;

3e) (syn, anti)-4-{1-(4-(10,11-difluorocyclopropyldibenzo- suber-5-yl)piperazin-1-yl)prop-3-ylthio[]indole, or a pharmaceutically acceptable salt or solvate thereof;

3f) (syn, anti)-4-{1-(4-(10,11-difluorocyclopropyldibenzo- suber-5-yl)piperazin-1-yl)but-4-ylthio}indole, or a pharmaceutically acceptable salt or solvate thereof;

3g) (syn, anti)-4-{1-(4-(10,11-difluorocyclopropyldibenzo- suber-5-yl)piperazin-1-yl)eth-2-ylsulfinyl}indole, or a pharmaceutically acceptable salt or solvate thereof;

3h) (syn, anti)-4-{1-(4-(10,11-difluorocyclopropyldibenzo- suber-5-yl)piperazin-1-yl)prop-3-ylsulfinyl}indole, or a pharmaceutically acceptable salt or solvate thereof;

3i) (syn, anti)-4-{1-(4-(10,11-difluorocyclopropyldibenzo- suber-5-yl)piperazin-1-yl)but-4-ylsulfinyl}indole, or a pharmaceutically acceptable salt or solvate thereof;

3j) (syn, anti)-4-{1-(4-(10,11-difluorocyclopropyldibenzo- suber-5-yl)piperazin-1-yl)eth-2-ylsulfonyl}indole, or a pharmaceutically acceptable salt or solvate thereof;

3k) (syn, anti)-4-{1-(4-(10,11-difluorocyclopropyldibenzo- suber-5-yl)piperazin-1-yl)prop-3-ylsulfonyl}indole, or a pharmaceutically acceptable salt or solvate thereof;

3l) (syn, anti)-4-{1-(4-(10,11-difluorocyclopropyldibenzo- suber-5-yl)piperazin-1-yl)but-4-ylsulfonyl}indole, or a pharmaceutically acceptable salt or solvate thereof;

3m) (syn, anti)-4-(1-(4-(10,11-difluorocyclopropyldibenzo- suber-5-yl)piperazin-1-yl)-2(R,S)-hydroxybut-4-yl}indole, or a pharmaceutically acceptable salt or solvate thereof;

3n) (syn, anti)-4-{1-(4-(10,11-difluorocyclopropyldibenzo- suber-5-yl)piperazin-1-yl)-2(R,S)-hydroxypent-5-yl}indole, or a pharmaceutically acceptable salt or solvate thereof;

3o) (syn, anti)-4-{1-(4-(10,11-difluorocyclopropyldibenzo- suber-5-yl)piperazin-1-yl)-2(R,S)-hydroxyprop-3- ylthio}indole, or a pharmaceutically acceptable salt or solvate thereof;

3p) (syn, anti)-4-{1-(4-(10,11-difluorocyclopropyldibenzo- suber-5-yl)piperazin-1-yl)-2(R,S)-hydroxybut-4- ylthio}indole, or a pharmaceutically acceptable salt or solvate thereof;

3q) (syn, anti)-4-{1-(4-(10,11-difluorocyclopropyldibenzo- suber-5-yl)piperazin-1-yl)-2(R,S)-hydroxyprop-3- ylsulfinyl}indole, or a pharmaceutically acceptable salt or solvate thereof;

3r) (syn, anti)-4-{1-(4-(10,11-difluorocyclopropyldibenzo- suber-5-yl)piperazin-1-yl)-2(R,S)-hydroxybut-4- ylsulfinyl}indole, or a pharmaceutically acceptable salt or solvate thereof;

3s) (syn, anti)-4-{1-(4-(10,11-difluorocyclopropyldibenzo- suber-5-yl)piperazin-1-yl)-2(R,S)-hydroxyprop-3- ylsulfonyl}indole, or a pharmaceutically acceptable salt or solvate thereof;

3t) (syn, anti)-4-{1-(4-(10,11-difluorocyclopropyldibenzo- suber-5-yl)piperazin-1-yl)-2(R,S)-hydroxybut-4- ylsulfonyl}indole, or a pharmaceutically acceptable salt or solvate thereof;

3u) (syn, anti)-4-{1-(4-(10,11-difluorocyclopropyldibenzo- suber-5-yl)piperazin-1-yl)-2(R,S)-oxy($C_1$–$C_6$ alkanoyl)but-4- yl}indole, or a pharmaceutically acceptable salt or solvate thereof;

3v) (syn, anti)-4-{1-(4-(10,11-difluorocyclopropyldibenzo- suber-5-yl)piperazin-1-yl)-2(R,S)-oxy($C_1$–$C_6$ alkanoyl)pent- 5-yl}indole, or a pharmaceutically acceptable salt or solvate thereof;

3w) (syn, anti)-4-{1-(4-(10,11-difluorocyclopropyldibenzo- suber-5-yl)piperazin-1-yl)-2(R,S)-oxycarbonyl($C_1$–$C_6$ alkanoxy)but-4-yl}indole, or a pharmaceutically acceptable salt or solvate thereof;

3x) (syn, anti)-4-{1-(4-(10,11-difluorocyclopropyldibenzo- suber-5-yl)piperazin-1-yl)-2(R,S)-oxycarbonyl($C_1$–$C_6$ alkanoxy)pent-5-yl}indole, or a pharmaceutically acceptable salt or solvate thereof;

3y) (syn, anti)-4-{1-(4-(10,11-difluorocyclopropyldibenzo- suber-5-yl)piperazin-1-yl)-2(R,S)-oxycarbonyloxy($C_1$–$C_6$ alkandiyl)carbonyl ($C_1$–$C_6$ alkanoxy)but-4-yl[]indole, or a pharmaceutically acceptable salt or solvate thereof;

3z) (syn, anti)-4-{1-(4-(10,11-difluorocyclopropyldibenzo- suber-5-yl)piperazin-1-yl)-2(R,S)-oxycarbonyloxy($C_1$–$C_6$ alkandiyl)carbonyl ($C_1$–$C_6$ alkanoxy)pent-5-yl}indole, or a pharmaceutically acceptable salt or solvate thereof;

3aa) (syn, anti)-4-{1-(4-(10,11-difluorocyclopropyldibenzo- suber-5-yl)piperazin-1-yl)-2(R,S)-oxycarbonyloxy($C_1$–$C_6$ alkandiyl) carboxybut-4-yl}indole, or a pharmaceutically acceptable salt or solvate thereof;

3bb) (syn, anti)-4-{1-(4-(10,11-difluorocyclopropyldibenzo- suber-5-yl)piperazin-1-yl)-2(R,S)-oxycarbonyloxy($C_1$–$C_6$ alkandiyl) carboxypent-5-yl}indole, or a pharmaceutically acceptable salt or solvate thereof;

3cc) (syn, anti)-4-{1-(4-(10,11-difluorocyclopropyldibenzo- suber-5-yl)piperazin-1-yl)-2(R,S)-oxycarbonyl($C_1$–$C_6$ alkandiyl)carboxybut-4-yl}indole, or a pharmaceutically acceptable salt or solvate thereof;

3dd) (syn, anti)-4-{1-(4-(10,11-difluorocyclopropyldibenzo- suber-5-yl)piperazin-1-yl)-2(R,S)-oxycarbonyl($C_1$–$C_6$ alkandiyl)carbonyl ($C_1$–$C_6$ alkanoxy)pent-5-yl}indole, or a pharmaceutically acceptable salt or solvate thereof;

4a) (syn, anti)-1-{1-(4-(10,11-difluorocyclopropyldibenzo-suber-5-yl)piperazin-1-yl)prop-3-yl)naphthalene, or a pharmaceutically acceptable salt or solvate thereof;

4b) (syn, anti)-1-{1-(4-(10,11-difluorocyclopropyldibenzo- suber-5-yl)piperazin-1- yl)but-4-yl}naphthalene, or a pharmaceutically acceptable salt or solvate thereof;

4c) (syn, anti)-1-(1-(4-(10,11-difluorocyclopropyldibenzo- suber-5-yl)piperazin-1-yl)pent-5-yl}naphthalene, or a pharmaceutically acceptable salt or solvate thereof;

4d) (syn, anti)-1-{1-(4-(10,11-difluorocyclopropyldibenzo- suber-5-yl)piperazin-1-yl)eth-2-ylthio}naphthalene, or a pharmaceutically acceptable salt or solvate thereof;

4e) (syn, anti)-1-{1-(4-(10,11-difluorocyclopropyldibenzo-suber-5-yl)piperazin-1-yl)prop-3-ylthio[]naphthalene, or a pharmaceutically acceptable salt or solvate thereof;

4f) (syn, anti)-1-{1-(4-(10,11-difluorocyclopropyldibenzo- suber-5-yl)piperazin-1-yl)but-4-ylthio[]naphthalene, or a pharmaceutically acceptable salt or solvate thereof;

4g) (syn, anti)-1-{1-(4-(10,11-difluorocyclopropyldibenzo- suber-5-yl)piperazin-1-yl)eth-2-ylsulfinyl}naphthalene, or a pharmaceutically acceptable salt or solvate thereof;

4h) (syn, anti)-1-{1-(4-(10,11-difluorocyclopropyldibenzo- suber-5-yl)piperazin-1-yl)prop-3-ylsulfinyl[]naphthalene, or a pharmaceutically acceptable salt or solvate thereof;

4i) (syn, anti)-1-{1-(4-(10,11-difluorocyclopropyldibenzo- suber-5-yl)piperazin-1-yl)but-4-ylsulfinyl}naphthalene, or a pharmaceutically acceptable salt or solvate thereof;

4j) (syn, anti)-1-{1-(4-(10,11-difluorocyclopropyldibenzo-suber-5-yl)piperazin-1-yl)eth-2-ylsulfonyl}naphthalene, or a pharmaceutically acceptable salt or solvate thereof;

4k) (syn, anti)-1-{1-(4-(10,11-difluorocyclopropyldibenzo- suber-5-yl)piperazin-1-yl)prop-3-ylsulfonyl}naphthalene, or a pharmaceutically acceptable salt or solvate thereof;

4l) (syn, anti)-1-{1-(4-(10,11-difluorocyclopropyldibenzo- suber-5-yl)piperazin-1-yl)but-4-ylsulfonyl}naphthalene, or a pharmaceutically acceptable salt or solvate thereof;

4m) (syn, anti)-1-{1-(4-(10,11-difluorocyclopropyldibenzo- suber-5-yl)piperazin-1-yl)-2(R,S)-hydroxybut-4- yl}naphthalene, or a pharmaceutically acceptable salt or solvate thereof;

4n) (syn, anti)-1-{1-(4-(10,11-difluorocyclopropyldibenzo- suber-5-yl)piperazin-1-yl)-2(R,S)-hydroxypent-5- yl}naphthalene, or a pharmaceutically acceptable salt or solvate thereof;

4o) (syn, anti)-1-({-(4-(10,11-difluorocyclopropyldibenzo- suber-5-yl)piperazin-1-yl)-2(R,S)-hydroxyprop-3- ylthio}naphthalene, or a pharmaceutically acceptable salt or solvate thereof;

4p) (syn, anti)-1-{1-(4-(10,11-difluorocyclopropyldibenzo- suber-5-yl)piperazin-1-yl)-2(R,S)-hydroxybut-4- ylthioynaphthalene, or a pharmaceutically acceptable salt or solvate thereof;

4q) (syn, anti)-1-{1-(4-(10,11-difluorocyclopropyldibenzo- suber-5-yl)piperazin-1-yl)-2(R,S)-hydroxyprop-3- ylsulfinyllnaphthalene, or a pharmaceutically acceptable salt or solvate thereof;

4r) (syn, anti)-1-{1-(4-(10,11-difluorocyclopropyldibenzo- suber-5-yl)piperazin-1-yl)-2(R,S)-hydroxybut-4- ylsulfinyl)naphthalene, or a pharmaceutically acceptable salt or solvate thereof;

4s) (syn, anti)-1-{1-(4-(10,11-difluorocyclopropyldibenzo- suber-5-yl)piperazin-1-yl)-2(R,S)-hydroxyprop-3- ylsulfonyl}naphthalene, or a pharmaceutically acceptable salt or solvate thereof;

4t) (syn, anti)-1-{1-(4-(10,11-difluorocyclopropyldibenzo- suber-5-yl)piperazin-1-yl)-2(R,S)-hydroxybut-4-ylsulfonyl}- naphthalene, or a pharmaceutically acceptable salt or solvate thereof;

4u) (syn, anti)-1-(1-(4-(10,11-difluorocyclopropyldibenzo- suber-5-yl)piperazin-1-yl)-2(R,S)-oxy($C_1-C_6$ alkanoyl)but-4- yllnaphthalene, or a pharmaceutically acceptable salt or solvate thereof;

4v) (syn, anti)-1-(1-(4-(10,11-difluorocyclopropyldibenzo- suber-5-yl)piperazin-1-yl)-2(R,S)-oxy(CI-$C_6$ alkanoyl)pent-5-yl}naphthalene, or a pharmaceutically acceptable salt or solvate thereof;

4w) (syn, anti)-1-{1-(4-(10,11-difluorocyclopropyldibenzo- suber-5-yl)piperazin-1-yl)-2(R,S)-oxycarbonyl($C_1-C_6$ alkanoxy)but-4-yl}naphthalene, or a pharmaceutically acceptable salt or solvate thereof;

4x) (syn, anti)-1-{1-(4-(10,11-difluorocyclopropyldibenzo- suber-5-yl)piperazin-1-yl)-2(R,S)-oxycarbonyl($C_1-C_6$ alkanoxy)pent-5-yl}naphthalene, or a pharmaceutically acceptable salt or solvate thereof;

4y) (syn, anti)-1-{1-(4-(10,11-difluorocyclopropyldibenzo- suber-5-yl)piperazin-1-yl)-2(R,S)-oxycarbonyloxy($C_1-C_6$ alkandiyl)carbonyl ($C_1-C_6$ alkanoxy)but-4-yl}naphthalene, or a pharmaceutically acceptable salt or solvate thereof;

4z) (syn, anti)-1-{1-(4-(10,11-difluorocyclopropyldibenzo- suber-5-yl)piperazin-1-yl)-2(R,S)-oxycarbonyloxy($C_1-C_6$ alkandiyl)carbonyl ($C_1-C_6$ alkanoxy)pent-5-yl}naphthalene, or a pharmaceutically acceptable salt or solvate thereof;

4aa) (syn, anti)-1-{1-(4-(10,11-difluorocyclopropyldibenzo- suber-5-yl)piperazin-1-yl)-2(R,S)-oxycarbonyloxy($C_1-C_6$ alkandiyl) carboxybut-4-yl}naphthalene, or a pharmaceutically acceptable salt or solvate thereof;

4bb) (syn, anti)-1-(1-(4-(10,11-difluorocyclopropyldibenzo- suber-5-yl)piperazin-1-yl)-2(R,S)-oxycarbonyloxy($C_1-C_6$ alkandiyl) carboxypent-5-yl}naphthalene, or a pharmaceutically acceptable salt or solvate thereof;

4cc) (syn, anti)-1-{1-(4-(10,11-difluorocyclopropyldibenzo- suber-5-yl)piperazin-1-yl)-2(R,S)-oxycarbonyl($C_1-C_6$ alkandiyl)carboxybut-4-yl}naphthalene, or a pharmaceutically acceptable salt or solvate thereof;

4dd) (syn, anti)-1-{1-(4-(10,11-difluorocyclopropyldibenzo- suber-5-yl)piperazin-1-yl)-2(R,S)-oxycarbonyl($C_1-C_6$ alkandiyl)carbonyl ($C_1-C_6$ alkanoxy)pent-5-yl}naphthalene, or a pharmaceutically acceptable salt or solvate thereof; and mixtures thereof.

4. A compound of claim 1 which is: anti-5-{1-(4-(10,11-difluorocyclopropyldibenzosuber-5-yl) piperazin-1-yl)-2(R, S)-hydroxybut-4-yl}quinoline or a pharmaceutically acceptable salt or solvate thereof.

5. The trihydrochloride salt of a compound of claim 4.

6. A compound of claim 1 which is: anti-5-{1-(4-(10,11-difluorocyclopropyldibenzosuber-5-yl)piperazin-1-yl)-2(R)-hydroxyprop-3-ylthio}quinoline or a pharmaceutically acceptable salt or solvate thereof.

7. The trihydrochloride salt of the compound of claim 6.

8. A pharmaceutical composition comprising a compound or salt or solvate of claim 1 in association with a pharmaceutically acceptable carrier, diluent, or excipient.

9. A pharmaceutical composition of claim 8 which also includes a cancer treatment drug.

10. A pharmaceutical composition of claim 8 which also includes a malaria treatment drug.

11. A method of treatment for a drug resistant disease comprising coadministering to a mammal in need thereof a resistance modulating amount of a compound or salt or solvate of claim 1 and an effective amount of a treatment drug for said drug resistant disease.

12. A method of treatment for a multidrug resistant disease comprising coadministering to a mammal in need thereof a multidrug resistance modulating amount of a compound or salt or solvate of claim 1 and an effective amount of a treatment drug for said multidrug resistant disease.

13. The method of claim 11 in which the drug resistance is caused by the action of P-glycoprotein.

14. The method of claim 11 in which said drug resistant disease is cancer and said treatment drug is a cancer chemotherapeutic drug or drugs.

15. The method of claim 11 in which said drug resistant disease is malaria, and said treatment drug is an anti-malarial drug or drugs.

16. The method of claim 12 in which said multidrug resistant disease is cancer and said treatment drug is a cancer chemotherapeutic drug or drugs.

17. A method for enhancing bioavailability of a drug to the brain comprising coadministering to a mammal in need thereof a therapeutically effective amount of said drug and an amount of a compound or salt or solvate of claim 1 sufficient to allow said drug to cross the blood-brain barrier and enter the brain.

18. A method for enhancing oral bioavailability of a drug comprising coadministering to a mammal in need thereof a therapeutically effective amount of said drug and an amount of a compound or salt or solvate of claim 1 sufficient to allow said drug to be transported across the gastrointestinal tract and enter the bloodstream.

* * * * *

UNITED STATES PATENT AND TRADEMARK OFFICE
CERTIFICATE OF CORRECTION

PATENT NO. : 5,776,939      Page 1 of 2

DATED : July 7, 1998

INVENTOR(S) : Julian Stanley Kroin and Bryan Hurst Norman

It is certified that error appears in the above-identified patent and that said Letters Patent is hereby corrected as shown below:

Column 34, line 41 reads ..."or —$R^5$;, and should be removed.

Column 34, line 42 reads..."—$R^5$ is"... and should be removed.

Column 34, line 43 reads... "—$R^6$ is $C_1$-$C_4$ or" ...and should read — —$R^6$ is $C_1$-$C_6$ alkyl or—

Column 35, line 23 reads... "suber-5-yl)piperazin-1-yl)but-4-ylthiolquinoline, or a" ... and should read — suber-5-yl)piperazin-1-yl) but-4-ylthio}quinoline, or a—

Column 36, line 21 reads... "yl)-2(R,S)-oxy($c_1$-$C_6$ alkanoyl)pent- 5-yllquinoline,"... and should read
— yl)-2(R,S)-oxy($C_1$-$C_6$ alkanoyl)pent-5-yl}quinoline, —

Column 37, line 19 reads... "yl)but-4-ylthioyisoquinoline, or a pharmaceutically"... and should read — yl)but-4-ylthio}isoquinoline, or a pharmaceutically—

Column 37, line 28 reads... "yl)prop-3-ylsulfinyllisoquinoline, or a pharmaceuti-"... and should read — yl)prop-3-ylsulfinyl} isoquinoline, or a pharmaceuti- —

Column 38, line 7 reads... "yl)-2(R,S)-hydroxyprop-3-ylsulfonylyisoquinoline, or" ... and should read — yl) -2 (R,S) – hydroxyprop-3-ylsulfonyl} isoquinoline, or—

Column 38, line 31 reads... "yllisoquinoline, or a pharmaceutically acceptable salt" ... and should read — yl}isoquinoline, or a pharmaceutically acceptable salt—

Column 39, line 3 reads... "yl)but-4-yllindole, or a pharmaceutically acceptable" ... and should read — yl) but-4-yl}indole, or a pharmaceutically acceptable—

Column 39, line 11 reads... "yl) eth-2-ylthiolindole, or a pharmaceutically accept-"... and should read — yl)eth-2-ylthio}indole, or a pharmaceutically accept- —

UNITED STATES PATENT AND TRADEMARK OFFICE
CERTIFICATE OF CORRECTION

PATENT NO. : 5,776,939

DATED : July 7, 1998

INVENTOR(S) : Julian Stanley Kroin and Bryan Hurst Norman

It is certified that error appears in the above-identified patent and that said Letters Patent is hereby corrected as shown below:

Column 39, line 16 reads... "yl)prop-3-ylthio[]indole, or a pharmaceutically"... and should read -- yl)prop-3-ylthio}indole, or a pharmaceutically--

Column 39, line 45 reads... "yl)but-4-ylsulfonyl]indole, or a pharmaceutically"... and should read -- yl) but-4-ylsulfonyl}indole, or a pharmaceutically--

Column 39, line 49 reads... "yl)-2(R,S)-hydroxybut-4-yl]indole, or a pharmaceuti-"... and should read -- yl) -2(R,S) - hydroxybut-4-yl}indole, or a pharmaceuti- --

Column 39, line 66 reads... "yl)-2(R,S)-hydroxyprop-3-ylsulfinyl]indole, or a phar-"... and should read -- yl) -2(R,S) - hydroxyprop-3-ylsulfinyl}indole, or a phar- --

Column 40, line 35 reads... "($C_1$-$C_6$ alkanoxy)but-4-yl[]indole, or a"... and should read -- ($C_1$-$C_6$ alkanoxy) but-4-yl}indole, or a--

Column 41, line 13 reads... "ylthio[]naphthalene, or a pharmaceutically accept-"... and should read -- ylthio}naphthalene, or a pharmaceutically accept- --

Column 41, line 18 reads... "yl)but-4-ylthio[]naphthalene, or a pharmaceutically"... and should read -- yl) but-4-ylthio}naphthalene, or a pharmaceutically--

Column 41, line 26 reads... "yl)prop-3-ylsulfinyl[]naphthalene, or a pharmaceu-"... and should read -- yl)prop-3-ylsulfinyl}naphthalene, or a pharmaceu- --

Column 41, line 64 reads... "yl)-2(R,S)-hydroxyprop-3-ylsulfinyl]naphthalene, or a"... and should read -- yl) -2(R,S) - hydroxyprop-3-ylsulfinyl}naphthalene, or a--

Column 42, line 13 reads... "yl)-2(R,S)-oxy($C_1$-$C_6$ alkanoyl)but-4-yl]naphthalene,"... and should read -- yl)-2(R,S)-oxy($C_1$-$C_6$ alkanoyl) but-4- yl}naphthalene,--

Signed and Sealed this

First Day of February, 2000

Attest:

Attesting Officer

Q. TODD DICKINSON

Acting Commissioner of Patents and Trademarks